United States Patent
Verdin et al.

(10) Patent No.: US 7,884,081 B2
(45) Date of Patent: Feb. 8, 2011

(54) METHODS OF MODULATING TUBULIN DEACETYLAST ACTIVITY

(75) Inventors: Eric M. Verdin, San Francisco, CA (US); Brian J. North, San Francisco, CA (US); Scott M. Ulrich, Ithaca, NY (US)

(73) Assignee: The J. David Gladstone Institutes, Irvine, CA (US)

( * ) Notice: Subject to any disclaimer, the term of this patent is extended or adjusted under 35 U.S.C. 154(b) by 296 days.

(21) Appl. No.: 12/029,333

(22) Filed: Feb. 11, 2008

(65) Prior Publication Data

US 2009/0005328 A1  Jan. 1, 2009

Related U.S. Application Data

(62) Division of application No. 10/441,854, filed on May 19, 2003, now Pat. No. 7,351,542.

(60) Provisional application No. 60/382,218, filed on May 20, 2002.

(51) Int. Cl.
*A01N 43/04* (2006.01)
*A01N 43/62* (2006.01)
*A61K 31/535* (2006.01)
*C12N 9/00* (2006.01)
*C12N 5/00* (2006.01)
*C12Q 1/34* (2006.01)

(52) U.S. Cl. ............ 514/43; 514/220; 514/230.5; 435/183; 435/375; 435/18; 435/19; 435/7.1

(58) Field of Classification Search ............ None
See application file for complete search history.

(56) References Cited

FOREIGN PATENT DOCUMENTS

| WO | WO 89/06132 A1 | 7/1989 |
| WO | WO 03/004621 A2 | 1/2003 |
| WO | WO 03/046207 * | 6/2003 |

OTHER PUBLICATIONS

Finnin et al. Structure of the histone deacetylase SIRT2. Nature Structural Biology. 2001, vol. 8, pp. 621-625.

Frye, R.A. Characterization of five human cDNAs with homology to the yeast SIR2 gene: Sir2-like proteins (sirtuins) metabolize NAD and may have protein ADP-ribosyltransferase activity. Biochemical and Biophysical Research Communications. 1999, vol. 260, pp. 273-279.

Grozinger, et al. Identification of a class of small molecule inhibitors of the sirtuin family of NAD-dependent deactylases by phenotypic screening. Journal of Biological Chemistry. 2001, vol. 276, No. 42, pp. 38837-38843.

Landry et al. Role of NAD(+) in the deacetylase activity of the SIR2-like proteins. Biochemical and Biophysical Research Communications. 2000, vol. 278, pp. 685-690.

Ledizet et al. Identification of an acetylation site of Chlamydomonas alpha-tubulin. Proc Natl Acad Sci USA. 1987, vol. 84, No. 16, pp. 5720-5724.

Li, Q., et al. Discovery and developments of antimitotic agents that inhibit tubulin polymerization for the treatment of cancer. Expert Opinion on Therapeutic Patents, Ashely Publications, GB, vol. 12, No. 11, Nov. 1, 2002, pp. 1663-1702.

Macrae, T. Tubulin post-translational modifications—enzymes and their mechanisms of action. European Journal of Biochemistry. 1997, vol. 244, pp. 265-278.

Maruta, H., et al. The acetylation of alpha-tubulin and its relationship to the assembly and disassembly of microtubules. Journal of Cell Biology. 1986, vol. 103, No. 2, pp. 571-579.

North, B., et al. The human Sir2 ortholog, SIRT2, is an NAD+-dependent tubulin deacetylase. Molecular Cell. 2003, vol. 11, No. 2, pp. 437-444.

Tanner et al. Silent information regulator 2 family of NAD- dependent histone/protein deacetylases generates a unique product, 1-O-acetyl-ADP-ribose. Proc Natl Acad Sci USA. 2000, vol. 97, pp. 14178-14182.

Smith et al. A phylogenetically conserved NAD+-dependent protein deacetylase activity in the Sir2 protein family. Proc Natl Acad Sci USA. 2000, vol. 97, pp. 6658-6663.

* cited by examiner

*Primary Examiner*—Robert B Mondesi
*Assistant Examiner*—Iqbal H Chowdhury
(74) *Attorney, Agent, or Firm*—Paula A. Borden; Bozicevic, Field & Francis LLP

(57) ABSTRACT

The present invention provides methods for identifying agents that modulate a level or an activity of tubulin deacetylase polypeptide, as well as agents identified by the methods. The invention further provides methods of modulating tubulin deacetylase activity in a cell. The invention further provides methods of modulating cellular proliferation by modulating the activity of tubulin deacetylase.

14 Claims, 8 Drawing Sheets

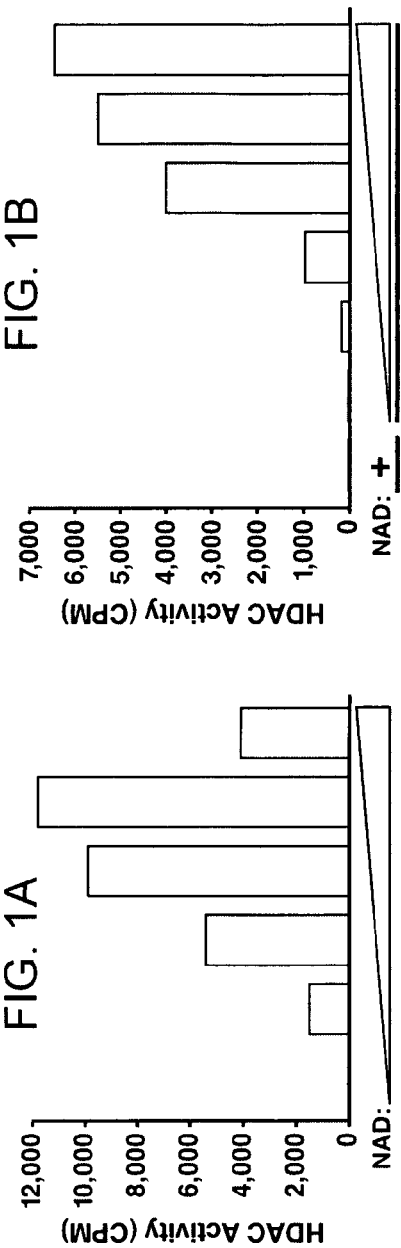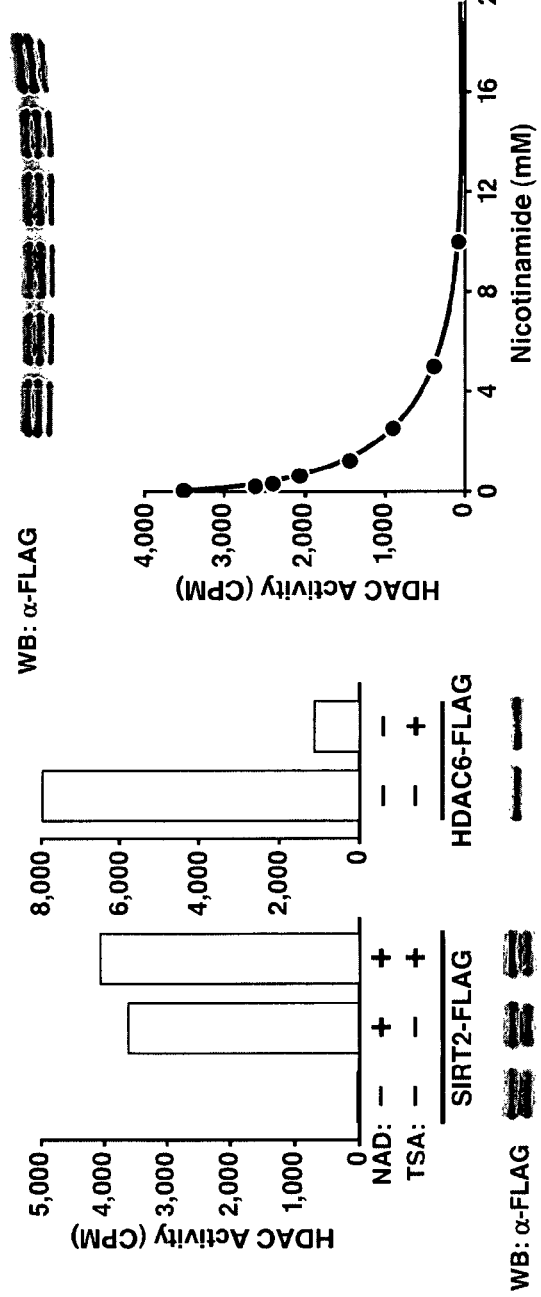

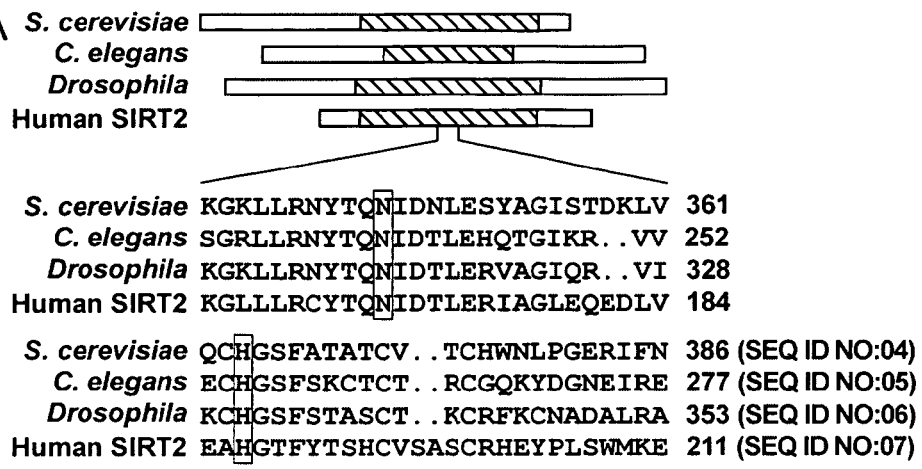

FIG. 2A

| | | |
|---|---|---|
| S. cerevisiae | KGKLLRNYTQNIDNLESYAGISTDKLV | 361 |
| C. elegans | SGRLLRNYTQNIDTLEHQTGIKR..VV | 252 |
| Drosophila | KGKLLRNYTQNIDTLERVAGIQR..VI | 328 |
| Human SIRT2 | KGLLLRCYTQNIDTLERIAGLEQEDLV | 184 |

| | | |
|---|---|---|
| S. cerevisiae | QCHGSFATATCV..TCHWNLPGERIFN | 386 (SEQ ID NO:04) |
| C. elegans | ECHGSFSKCTCT..RCGQKYDGNEIRE | 277 (SEQ ID NO:05) |
| Drosophila | KCHGSFSTASCT..KCRFKCNADALRA | 353 (SEQ ID NO:06) |
| Human SIRT2 | EAHGTFYTSHCVSASCRHEYPLSWMKE | 211 (SEQ ID NO:07) |

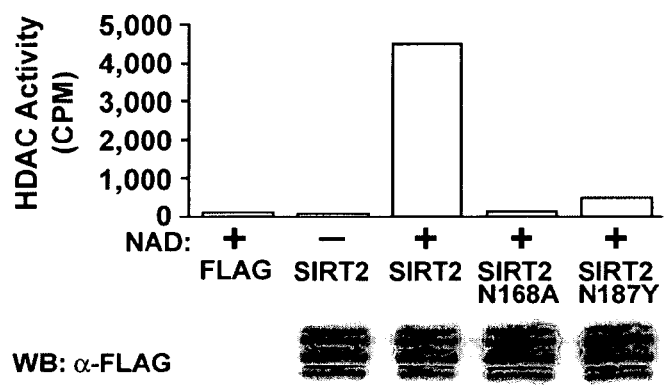

FIG. 2B

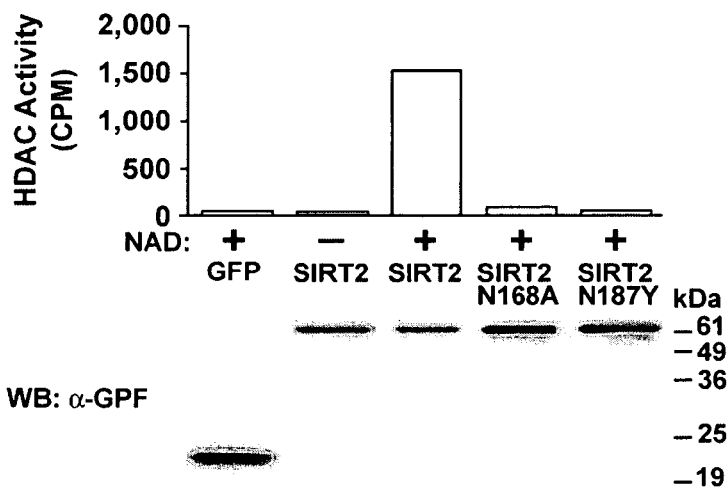

FIG. 2C

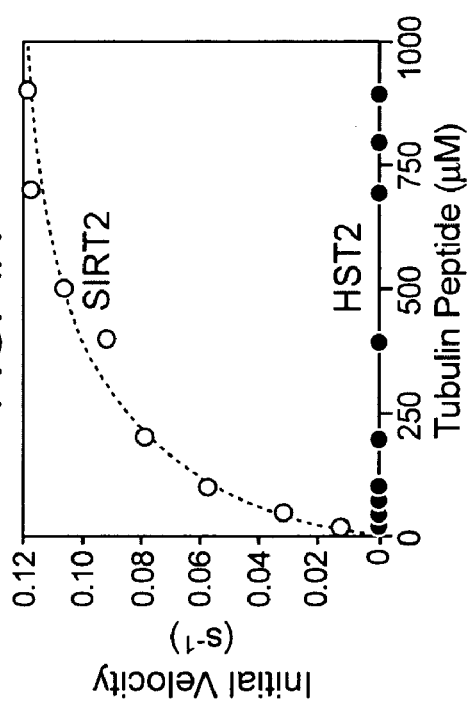
FIG. 4A
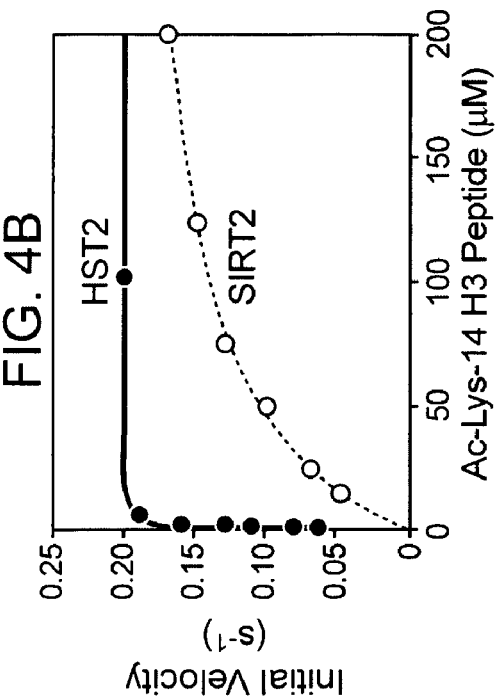
FIG. 4B
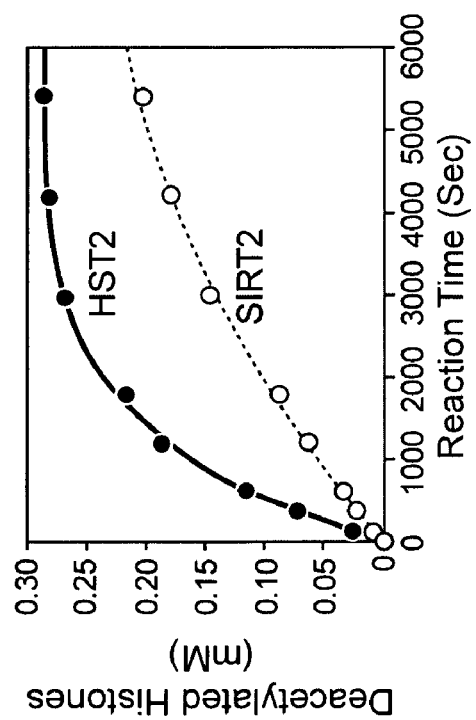
FIG. 4C
| | SIRT2 | HST2 |
|---|---|---|
| Acetylated Tubulin Peptide | $K_{cat}$ 0.144 ±0.05 s⁻¹ | 0.00254 ±0.0003 s⁻¹ |
| | $V/K$ 894 ±100 M⁻¹s⁻¹ | 14.9 ±5.4 M⁻¹s⁻¹ |
| Acetylated Histone H3 Peptide | $K_m$ 54.2±3.6 μM | ±0.014 μM |
| | $V/K$ 3930 ±261 M⁻¹s⁻¹ | 717900 ±35900 M⁻¹s⁻¹ |
| | $K_{cat}$ 0.2 s⁻¹ | 0.2 s⁻¹ |
FIG. 4D

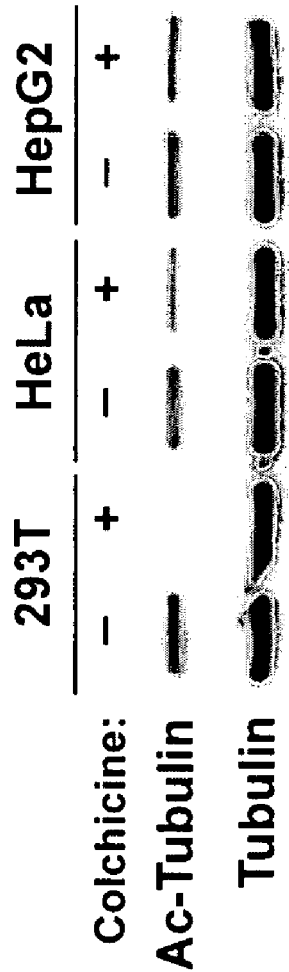
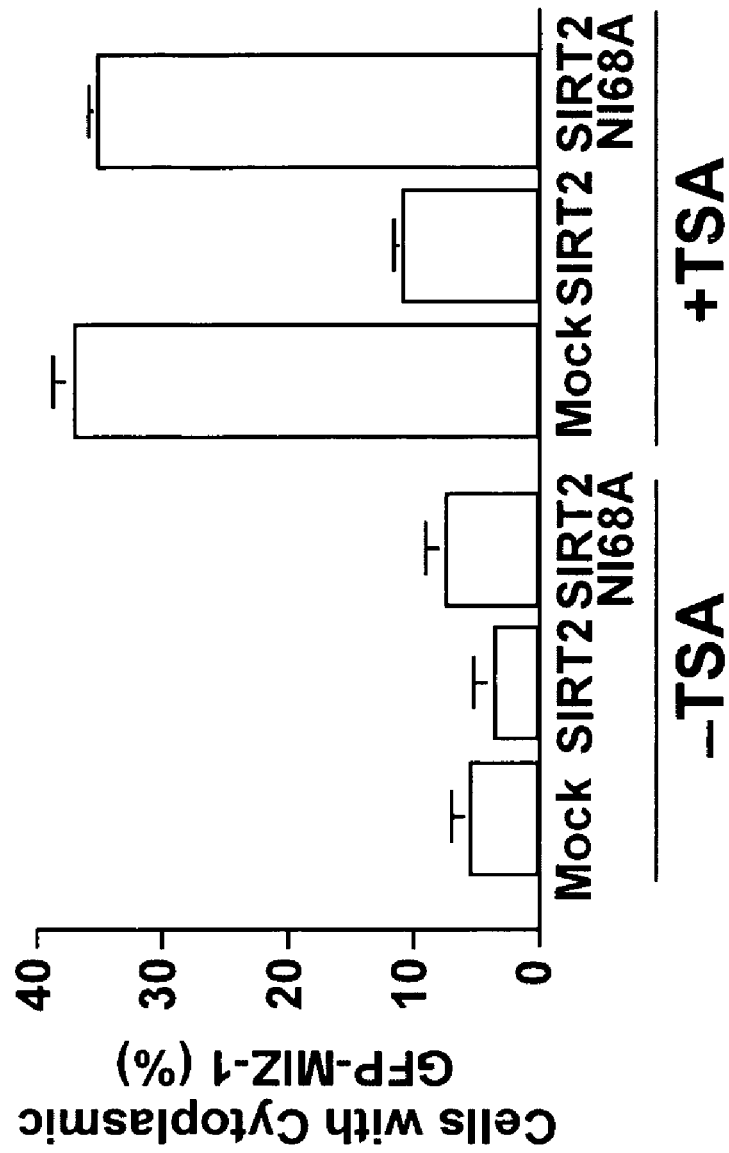
FIG. 5A
FIG. 5B

FIG. 6A
Human SIRT2 nucleotide sequence (SEQ ID NO:01)

```
   1 gtgttgtacg aaagcgcgtc tgcggccgca atgtctgctg agagttgtag ttctgtgccc
  61 tatcacggcc actcccattt ctggtgccgt cacgggacag agcagtcggt gacaggacag
 121 agcagtcggt gacgggacac agtggttggt gacgggacag agcggtcggt gacagcctca
 181 agggcttcag caccgcgccc atggcagagc cagacccctc tcaccctctg agacccagg
 241 cagggaaggt gcaggaggct caggactcag attcagactc tgagggagga gccgctggtg
 301 gagaagcaga catggacttc ctgcggaact tattctccca gacgctcagc ctgggcagcc
 361 agaaggagcg tctgctggac gagctgacct tggaagggt ggcccggtac atgcagagcg
 421 aacgctgtcg cagagtcatc tgtttggtgg gagctggaat ctccacatcc gcaggcatcc
 481 ccgactttcg ctctccatcc accggcctct atgacaacct agagaagtac catcttccct
 541 acccagaggc catctttgag atcagctatt tcaagaaaca tccggaaccc ttcttcgccc
 601 tcgccaagga actctatcct gggcagttca agccaaccat ctgtcactac ttcatgcgcc
 661 tgctgaagga caagggcta ctcctgcgct gctacacgca gaacatagat accctggagc
 721 gaatagccgg gctggaacag gaggacttgg tggagcgcca cggcaccttc tacacatcac
 781 actgcgtcag cgccagctgc cggcacgaat acccgctaag ctggatgaaa gagaagatct
 841 tctctgaggt gacgcccaag tgtgaagact gtcagagcct ggtgaagcct gatatcgtct
 901 ttttggtga gagcctccca gcgcgtttct tctcctgtat gcagtcagac ttcctgaagg
 961 tggacctcct cctggtcatg ggtacctcct gcaggtgca gcccttgcc tccctcatca
1021 gcaaggcacc cctctccacc cctcgcctgc tcatcaacaa ggagaaagct ggccagtcgg
1081 accctttcct ggggatgatt atgggcctcg gaggagcat ggactttgac tccaagaagg
1141 cctacaggga cgtggcctgg ctgggtgaat gcgaccaggg ctgcctggcc cttgctgagc
1201 tccttggatg gaagaaggag ctggaggacc ttgtccggag ggagcacgcc agcatagatg
1261 cccagtcggg ggcggggtc cccaacccca gcacttcagc ttcccccaag aagtccccgc
1321 cacctgccaa ggacgaggcc aggacaacag agagggagaa accccagtga cagctgcatc
1381 tcccaggcgg gatgccgagc tcctcaggga cagctgagcc caacccgggc ctggcccct
1441 cttaaccagc agttcttgtc tggggagctc agaacatccc ccaatctctt acagctccct
1501 ccccaaaact ggggtcccag caaccctggc cccaacccc agcaaatctc taacacctcc
1561 tagaggccaa ggcttaaaca ggcatctcta ccagccccac tgtctctaac cactcctggg
1621 ctaaggagta acctccctca tctctaactg ccccacggg gccagggcta ccccagaact
1681 tttaactctt ccaggacagg gagcttcggg ccccactct gtctcctgcc ccgggggcc
1741 tgtggctaag taaaccatac ctaacctacc ccagtgtggg tgtgggcctc tgaatataac
1801 ccacacccag cgtaggggga gtctgagccg ggagggctcc cgagtctctg ccttcagctc
1861 ccaaagtggg tggtgggccc ccttcacgtg ggacccactt cccatgctgg atgggcagaa
1921 gacattgctt attggagaca aattaaaaac aaaaacaact aac
```

FIG. 6B
Human SIRT2 amino acid sequence (SEQ ID NO:02)

MAEPDPSHPLETQAGKVQEAQDSDSDSEGGAAGGEADMDFLRNLFSQTLSLGSQKE
RLLDELTLEGVARYMQSERCRRVICLVGAGISTSAGIPDFRSPSTGLYDNLEKYHLPY
PEAIFEISYFKKHPEPFFALAKELYPGQFKPTICHYFMRLLKDKGLLLRCYTQNIDTLE
RIAGLEQEDLVEAHGTFYTSHCVSASCRHEYPLSWMKEKIFSEVTPKCEDCQSLVKP
DIVFFGESLPARFFSCMQSDFLKVDLLLVMGTSLQVQPFASLISKAPLSTPRLLINKEK
AGQSDPFLGMIMGLGGGMDFDSKKAYRDVAWLGECDQGCLALAELLGWKKELED
LVRREHASIDAQSGAGVPNPSTSASPKKSPPPAKDEARTTEREKPQ

SEQUENCE LISTING

<160> NUMBER OF SEQ ID NOS: 9

<210> SEQ ID NO 1
<211> LENGTH: 1963
<212> TYPE: DNA
<213> ORGANISM: Homo sapiens

<400> SEQUENCE: 1

```
gtgttgtacg aaagcgcgtc tgcggccgca atgtctgctg agagttgtag ttctgtgccc        60
tatcacggcc actcccattt ctggtgccgt cacgggacag agcagtcggt gacaggacag       120
agcagtcggt gacgggacac agtggttggt gacgggacag agcggtcggt gacagcctca       180
agggcttcag caccgcgccc atggcagagc cagaccccct tcaccctctg gagacccagg       240
```

-continued

```
caggga aggt gcaggaggct caggactcag attcagactc tgagggagga gccgctggtg   300
gagaagcaga catggacttc ctgcggaact tattctccca cgctcagc ctgggcagcc     360 agaaggagcg tctgctggac gagctgacct tggaaggggt ggcccggtac atgcagagcg   420
aacgctgtcg cagagtcatc tgtttggtgg gagctggaat ctccacatcc gcaggcatcc   480
ccgactttcg ctctccatcc accggcctct atgacaacct agagaagtac atcttccct   540 acccagaggc catctttgag atcagctatt tcaagaaaca tccggaaccc ttcttcgccc   600
tcgccaagga actctatcct gggcagttca agccaaccat ctgtcactac ttcatgcgcc   660
tgctgaagga caaggggcta ctcctgcgct gctacacgca gaacatagat accctggagc   720
gaatagccgg gctggaacag gaggacttgg tggaggcgca cggcaccttc tacacatcac   780
actgcgtcag cgccagctgc cggcacgaat acccgctaag ctggatgaaa gagaagatct   840
tctctgaggt gacgcccaag tgtgaagact gtcagagcct ggtgaagcct gatatcgtct   900 ttttggtga gagcctccca gcgcgtttct tctcctgtat gcagtcagac ttcctgaagg   960
tggacctcct cctggtcatg ggtacctcct tgcaggtgca gccctttgcc tccctcatca  1020
gcaaggcacc cctctccacc cctcgcctgc tcatcaacaa ggagaaagct ggccagtcgg  1080 acccttttcct ggggatgatt atgggcctcg gaggaggcat ggactttgac tccaagaagg  1140
cctacaggga cgtggcctgg ctgggtgaat gcgaccaggg ctgcctggcc cttgctgagc  1200
tccttggatg gaagaaggag ctggaggacc ttgtccggag ggagcacgcc agcatagatg  1260
cccagtcggg ggcggggggtc cccaaccccca gcacttcagc ttcccccaag aagtccccgc  1320
cacctgccaa ggacgaggcc aggacaacag agagggagaa accccagtga cagctgcatc  1380
tcccaggcgg gatgccgagc tcctcaggga cagctgagcc caaccgggc ctggcccccct  1440 cttaaccagc agttcttgtc tggggagctc agaacatccc ccaatctctt acagctccct  1500
cccaaaaact ggggtcccag caaccctggc ccccaacccc agcaaatctc taacacctcc  1560
tagaggccaa ggcttaaaca ggcatctcta ccagcccac tgtctctaac cactcctggg   1620
ctaaggagta acctccctca tctctaactg cccccacggg gccagggcta ccccagaact  1680
tttaactctt ccaggacagg gagcttcggg cccccactct gtctcctgcc cccggggggcc   1740 tgtggctaag taaaccatac ctaacctacc ccagtgtggg tgtgggcctc tgaatataac   1800
ccacacccag cgtaggggga gtctgagccg ggagggctcc cgagtctctg ccttcagctc   1860
ccaaagtggg tggtgggccc ccttcacgtg ggacccactt cccatgctgg atgggcagaa   1920
gacattgctt attggagaca aattaaaaac aaaaacaact aac                     1963
```

<210> SEQ ID NO 2
<211> LENGTH: 389
<212> TYPE: PRT
<213> ORGANISM: Homo sapiens

<400> SEQUENCE: 2

```
Met Ala Glu Pro Asp Pro Ser His Pro Leu Glu Thr Gln Ala Gly Lys
 1               5                  10                  15

Val Gln Glu Ala Gln Asp Ser Asp Ser Asp Ser Glu Gly Gly Ala Ala
             20                  25                  30

Gly Gly Glu Ala Asp Met Asp Phe Leu Arg Asn Leu Phe Ser Gln Thr
         35                  40                  45

Leu Ser Leu Gly Ser Gln Lys Glu Arg Leu Leu Asp Glu Leu Thr Leu
     50                  55                  60

Glu Gly Val Ala Arg Tyr Met Gln Ser Glu Arg Cys Arg Arg Val Ile
```

```
                65                  70                  75                  80
        Cys Leu Val Gly Ala Gly Ile Ser Thr Ser Ala Gly Ile Pro Asp Phe
                        85                  90                  95

Arg Ser Pro Ser Thr Gly Leu Tyr Asp Asn Leu Glu Lys Tyr His Leu
                        100                 105                 110

Pro Tyr Pro Glu Ala Ile Phe Glu Ile Ser Tyr Phe Lys Lys His Pro
                        115                 120                 125

Glu Pro Phe Phe Ala Leu Ala Lys Glu Leu Tyr Pro Gly Gln Phe Lys
                        130                 135                 140

Pro Thr Ile Cys His Tyr Phe Met Arg Leu Leu Lys Asp Lys Gly Leu
        145                 150                 155                 160

Leu Leu Arg Cys Tyr Thr Gln Asn Ile Asp Thr Leu Glu Arg Ile Ala
                        165                 170                 175

Gly Leu Glu Gln Glu Asp Leu Val Glu Ala His Gly Thr Phe Tyr Thr
                        180                 185                 190

Ser His Cys Val Ser Ala Ser Cys Arg His Glu Tyr Pro Leu Ser Trp
                        195                 200                 205

Met Lys Glu Lys Ile Phe Ser Glu Val Thr Pro Lys Cys Glu Asp Cys
                        210                 215                 220

Gln Ser Leu Val Lys Pro Asp Ile Val Phe Phe Gly Glu Ser Leu Pro
        225                 230                 235                 240

Ala Arg Phe Phe Ser Cys Met Gln Ser Asp Phe Leu Lys Val Asp Leu
                        245                 250                 255

Leu Leu Val Met Gly Thr Ser Leu Gln Val Gln Pro Phe Ala Ser Leu
                        260                 265                 270

Ile Ser Lys Ala Pro Leu Ser Thr Pro Arg Leu Leu Ile Asn Lys Glu
                        275                 280                 285

Lys Ala Gly Gln Ser Asp Pro Phe Leu Gly Met Ile Met Gly Leu Gly
                        290                 295                 300

Gly Gly Met Asp Phe Asp Ser Lys Lys Ala Tyr Arg Asp Val Ala Trp
        305                 310                 315                 320

Leu Gly Glu Cys Asp Gln Gly Cys Leu Ala Leu Ala Glu Leu Leu Gly
                        325                 330                 335

Trp Lys Lys Glu Leu Glu Asp Leu Val Arg Arg Glu His Ala Ser Ile
                        340                 345                 350

Asp Ala Gln Ser Gly Ala Gly Val Pro Asn Pro Ser Thr Ser Ala Ser
                        355                 360                 365

Pro Lys Lys Ser Pro Pro Ala Lys Asp Glu Ala Arg Thr Thr Glu
                        370                 375                 380

Arg Glu Lys Pro Gln
        385

<210> SEQ ID NO 3
<211> LENGTH: 20
<212> TYPE: PRT
<213> ORGANISM: Artificial Sequence
<220> FEATURE:
<223> OTHER INFORMATION: monoacetylated histone H3 peptide
<221> NAME/KEY: ACETYLATION
<222> LOCATION: (14)...(14)
<223> OTHER INFORMATION: Xaa = acetylated lysine
<221> NAME/KEY: VARIANT
<222> LOCATION: 14
<223> OTHER INFORMATION: Xaa = Any Amino Acid

<400> SEQUENCE: 3

Ala Arg Thr Lys Gln Thr Ala Arg Lys Ser Thr Gly Gly Xaa Ala Pro
```

```
                 1               5                  10                 15

Arg Lys Gln Leu
             20

<210> SEQ ID NO 4
<211> LENGTH: 52
<212> TYPE: PRT
<213> ORGANISM: S. cerevisiae

<400> SEQUENCE: 4

Lys Gly Lys Leu Leu Arg Asn Tyr Thr Gln Asn Ile Asp Asn Leu Glu
 1               5                  10                 15

Ser Tyr Ala Gly Ile Ser Thr Asp Lys Leu Val Gln Cys His Gly Ser
            20                  25                  30

Phe Ala Thr Ala Thr Cys Val Thr Cys His Trp Asn Leu Pro Gly Glu
        35                  40                  45

Arg Ile Phe Asn
    50

<210> SEQ ID NO 5
<211> LENGTH: 50
<212> TYPE: PRT
<213> ORGANISM: C. elegans

<400> SEQUENCE: 5

Ser Gly Arg Leu Leu Arg Asn Tyr Thr Gln Asn Ile Asp Thr Leu Glu
 1               5                  10                 15

His Gln Thr Gly Ile Lys Arg Val Val Glu Cys His Gly Ser Phe Ser
            20                  25                  30

Lys Cys Thr Cys Thr Arg Cys Gly Gln Lys Tyr Asp Gly Asn Glu Ile
        35                  40                  45

Arg Glu
    50

<210> SEQ ID NO 6
<211> LENGTH: 50
<212> TYPE: PRT
<213> ORGANISM: Drosophila

<400> SEQUENCE: 6

Lys Gly Lys Leu Leu Arg Asn Tyr Thr Gln Asn Ile Asp Thr Leu Glu
 1               5                  10                 15

Arg Val Ala Gly Ile Gln Arg Val Ile Glu Cys His Gly Ser Phe Ser
            20                  25                  30

Thr Ala Ser Cys Thr Lys Cys Arg Phe Lys Cys Asn Ala Asp Ala Leu
        35                  40                  45

Arg Ala
    50

<210> SEQ ID NO 7
<211> LENGTH: 54
<212> TYPE: PRT
<213> ORGANISM: H. sapiens

<400> SEQUENCE: 7

Lys Gly Leu Leu Leu Arg Cys Tyr Thr Gln Asn Ile Asp Thr Leu Glu
 1               5                  10                 15

Arg Ile Ala Gly Leu Glu Gln Glu Asp Leu Val Glu Ala His Gly Thr
            20                  25                  30
```

```
Phe Tyr Thr Ser His Cys Val Ser Ala Ser Cys Arg His Glu Tyr Pro
        35                  40                  45

Leu Ser Trp Met Lys Glu
        50

<210> SEQ ID NO 8
<211> LENGTH: 9
<212> TYPE: PRT
<213> ORGANISM: Artificial Sequence
<220> FEATURE:
<223> OTHER INFORMATION: synthetic a-tubulin peptide
<221> NAME/KEY: ACETYLATION
<222> LOCATION: (5)...(5)
<223> OTHER INFORMATION: Xaa = acetylated lysine
<221> NAME/KEY: VARIANT
<222> LOCATION: 5
<223> OTHER INFORMATION: Xaa = Any Amino Acid

<400> SEQUENCE: 8

Met Pro Ser Asp Xaa Thr Ile Gly Gly
  1               5

<210> SEQ ID NO 9
<211> LENGTH: 803
<212> TYPE: PRT
<213> ORGANISM: H. sapiens

<400> SEQUENCE: 9

Met Asp Phe Pro Gln His Ser Gln His Val Leu Glu Gln Leu Asn Gln
  1               5                  10                  15

Gln Arg Gln Leu Gly Leu Leu Cys Asp Cys Thr Phe Val Val Asp Gly
                 20                  25                  30

Val His Phe Lys Ala His Lys Ala Val Leu Ala Ala Cys Ser Glu Tyr
             35                  40                  45

Phe Lys Met Leu Phe Val Asp Gln Lys Asp Val Val His Leu Asp Ile
         50                  55                  60

Ser Asn Ala Ala Gly Leu Gly Gln Met Leu Glu Phe Met Tyr Thr Ala
 65                  70                  75                  80

Lys Leu Ser Leu Ser Pro Glu Asn Val Asp Asp Val Leu Ala Val Ala
                 85                  90                  95

Thr Phe Leu Gln Met Gln Asp Ile Ile Thr Ala Cys His Ala Leu Lys
            100                 105                 110

Ser Leu Ala Glu Pro Ala Thr Ser Pro Gly Gly Asn Ala Glu Ala Leu
        115                 120                 125

Ala Thr Glu Gly Gly Asp Lys Arg Ala Lys Glu Glu Lys Val Ala Thr
    130                 135                 140

Ser Thr Leu Ser Arg Leu Glu Gln Ala Gly Arg Ser Thr Pro Ile Gly
145                 150                 155                 160

Pro Ser Arg Asp Leu Lys Glu Glu Arg Gly Gly Gln Ala Gln Ser Ala
                165                 170                 175

Ala Ser Gly Ala Glu Gln Thr Glu Lys Ala Asp Ala Pro Arg Glu Pro
            180                 185                 190

Pro Pro Val Glu Leu Lys Pro Asp Pro Thr Ser Gly Met Ala Ala Ala
        195                 200                 205

Glu Ala Glu Ala Ala Leu Ser Glu Ser Ser Gln Glu Met Glu Val
    210                 215                 220

Glu Pro Ala Arg Lys Gly Glu Glu Gln Lys Glu Gln Glu Gln
225                 230                 235                 240

Glu Glu Glu Gly Ala Gly Pro Ala Glu Val Lys Glu Glu Gly Ser Gln
```

-continued

```
                245                 250                 255
Leu Glu Asn Gly Glu Ala Pro Glu Asn Glu Asn Glu Glu Ser Ala
            260                 265                 270
Gly Thr Asp Ser Gly Gln Glu Leu Gly Ser Glu Ala Arg Gly Leu Arg
        275                 280                 285
Ser Gly Thr Tyr Gly Asp Arg Thr Glu Ser Lys Ala Tyr Gly Ser Val
        290                 295                 300
Ile His Lys Cys Glu Asp Cys Gly Lys Glu Phe Thr His Thr Gly Asn
305                 310                 315                 320
Phe Lys Arg His Ile Arg Ile His Thr Gly Glu Lys Pro Phe Ser Cys
                325                 330                 335
Arg Glu Cys Ser Lys Ala Phe Ser Asp Pro Ala Ala Cys Lys Ala His
            340                 345                 350
Glu Lys Thr His Ser Pro Leu Lys Pro Tyr Gly Cys Glu Glu Cys Gly
        355                 360                 365
Lys Ser Tyr Arg Leu Ile Ser Leu Leu Asn Leu His Lys Lys Arg His
    370                 375                 380
Ser Gly Glu Ala Arg Tyr Arg Cys Glu Asp Cys Gly Lys Leu Phe Thr
385                 390                 395                 400
Thr Ser Gly Asn Leu Lys Arg His Gln Leu Val His Ser Gly Glu Lys
                405                 410                 415
Pro Tyr Gln Cys Asp Tyr Cys Gly Arg Ser Phe Ser Asp Pro Thr Ser
            420                 425                 430
Lys Met Arg His Leu Glu Thr His Asp Thr Lys Glu His Lys Cys
        435                 440                 445
Pro His Cys Asp Lys Lys Phe Asn Gln Val Gly Asn Leu Lys Ala His
    450                 455                 460
Leu Lys Ile His Ile Ala Asp Gly Pro Leu Lys Cys Arg Glu Cys Gly
465                 470                 475                 480
Lys Gln Phe Thr Thr Ser Gly Asn Leu Lys Arg His Leu Arg Ile His
                485                 490                 495
Ser Gly Glu Lys Pro Tyr Val Cys Ile His Cys Gln Arg Gln Phe Ala
            500                 505                 510
Asp Pro Gly Ala Leu Gln Arg His Val Arg Ile His Thr Gly Glu Lys
        515                 520                 525
Pro Cys Gln Cys Val Met Cys Gly Lys Ala Phe Thr Gln Ala Ser Ser
    530                 535                 540
Leu Ile Ala His Val Arg Gln His Thr Gly Glu Lys Pro Tyr Val Cys
545                 550                 555                 560
Glu Arg Cys Gly Lys Arg Phe Val Gln Ser Ser Gln Leu Ala Asn His
                565                 570                 575
Ile Arg His His Asp Asn Ile Arg Pro His Lys Cys Ser Val Cys Ser
            580                 585                 590
Lys Ala Phe Val Asn Val Gly Asp Leu Ser Lys His Ile Ile Ile His
        595                 600                 605
Thr Gly Glu Lys Pro Tyr Leu Cys Asp Lys Cys Gly Arg Gly Phe Asn
    610                 615                 620
Arg Val Asp Asn Leu Arg Ser His Val Lys Thr Val His Gln Gly Lys
625                 630                 635                 640
Ala Gly Ile Lys Ile Leu Glu Pro Glu Glu Gly Ser Glu Val Ser Val
                645                 650                 655
Val Thr Val Asp Asp Met Val Thr Leu Ala Thr Glu Ala Leu Ala Ala
            660                 665                 670
```

```
                -continued

Thr Ala Val Thr Gln Leu Thr Val Val Pro Val Gly Ala Ala Val Thr
        675                 680                 685

Ala Asp Glu Thr Glu Val Leu Lys Ala Glu Ile Ser Lys Ala Val Lys
    690                 695                 700

Gln Val Gln Glu Glu Asp Pro Asn Thr His Ile Leu Tyr Ala Cys Asp
705                 710                 715                 720

Ser Cys Gly Asp Lys Phe Leu Asp Ala Asn Ser Leu Ala Gln His Val
                725                 730                 735

Arg Ile His Thr Ala Gln Ala Leu Val Met Phe Gln Thr Asp Ala Asp
            740                 745                 750

Phe Tyr Gln Gln Tyr Gly Pro Gly Gly Thr Trp Pro Ala Gly Gln Val
        755                 760                 765

Leu Gln Ala Gly Glu Leu Val Phe Arg Pro Arg Asp Gly Ala Glu Gly
    770                 775                 780

Gln Pro Ala Leu Ala Glu Thr Ser Pro Thr Ala Pro Glu Cys Pro Pro
785                 790                 795                 800

Pro Ala Glu
```

METHODS OF MODULATING TUBULIN DEACETYLAST ACTIVITY

CROSS REFERENCE

This application is a divisional of U.S. patent application Ser. No. 10/441,854, filed May 19, 2003, which application claims the benefit of U.S. Provisional Patent Application No. 60/382,218, filed May 20, 2002, which applications are incorporated herein by reference in their entirety.

FIELD OF THE INVENTION

The present invention is in the field of deacetylase enzymes, and enzymes that modify tubulin.

BACKGROUND OF THE INVENTION

Reversible histone acetylation is under the control of opposing enzymatic activities of two categories of enzymes: histone deacetylases (HDACs) and histone acetyltransferases (HATs). Deacetylation of lysine residues on N-terminal tails of histones by HDACs is generally associated with transcriptional silencing, whereas acetylation of the same lysine residues is associated with transcriptional activation. In addition to histones, a rapidly growing number of other non-histone proteins undergo the post-translational modification of acetylation on lysine residues. An example of some of these proteins include HMG-14 and 17, HMGI(Y), p53, E2F1, NF-κB, and the HIV-1 Tat protein. HDACs are separated into three distinct classes based on their homology to yeast transcriptional repressors. Class I and Class II deacetylases are homologues of the Rpd3p and Hda1p proteins, respectively. Class III HDACs are defined based on their homology to the yeast transcriptional repressor, Sir2p.

The Silent Information Regulator (SIR) gene family was initially identified based on its role in the regulation of gene expression at the HM loci in *S. cerevisiae*. Later studies further defined the role of SIR proteins in transcriptional silencing at a number of additional loci in the yeast genome, including telomeres, rDNA locus, and at sites of DNA damage. Silencing at the telomeres and the HM loci, is mediated by a multi-protein complex which includes Sir2p, Sir3p and Sir4p, with Sir1p being involved in silencing at the HM loci only. Interestingly, silencing and repression of recombination at the rDNA locus is achieved by Sir2p in association with the RENT complex, containing Net1, Nan1 and cdc14, and has been associated with aging in *S. cerevisiae*. The recent discovery that SIR2 encodes an NAD-dependent histone deacetylase has validated the long held suspicion that this protein regulated the level of histone acetylation.

The SIR2 family of genes is conserved from archaebacteria to eukaryotes. In *S. cerevisiae*, this family consist of Sir2 and four closely related genes (HST1-4). Whereas Sir2p and HST1p are localized primarily in the nucleus, Hst2p is exclusively cytoplasmic. Humans have seven proteins with homology to the *S. cerevisiea* Sir2p, which have been named Sirtuins or SIRTs. Human SIRT1 and mouse Sir2α, which are most closely homologous to Sir2p and HST1p, exhibit protein deacetylase activity with specificity for the transcription factor protein p53. Deacetylation of p53 by SIRT1 suppresses p53-dependent apoptosis in response to DNA damage. The human SIRT2 protein, which is most closely related to Hst2p, is also localized in the cytoplasm. Interestingly, both SIRT2 and Hst2p regulate rDNA and telomeric silencing indirectly from their cytoplasmic location.

The microtubule network is formed by the polymerization of α/β tubulin heterodimers and plays an important role in the regulation of cell shape, intracellular transport, cell motility, and cell division. α and β tubulin sub-units are subject to numerous post-translational modifications including tyrosination, phosphorylation, polyglutamylation, polyglycylation and acetylation. Tubulin represents one of the major acetylated cytoplasmic proteins. Acetylation of tubulin takes place on lysine-40 of α-tubulin, which based on the crystal structure of the tubulin heterodimer, is predicted to lie within the luminal side of the polymerized microtubule.

A variety of physiological signals have been reported to modulate the level of tubulin acetylation. This includes the anticancer drug paclitaxel, as well as association of MAP1 and 2C, tau, and the herpes simplex virus encoded protein VP22. Similarly, microtubules associated with stable structures, such as cilia, contain relatively hyperacetylated α-tubulin. These observations have supported the notion that stabilized microtubules become hyperacetylated. However, the enzymes responsible for the reversible acetylation of tubulin have not been identified. This lack of reagents has precluded a thorough analysis of the biological role of tubulin acetylation in microtubule dynamics, stability and physiological functions of the cytoskeleton.

Literature

Frye (1999) *Biochem. Biophys. Res. Comm.* 260:273-279; Smith et al. (2000) *Proc. Natl. Acad. Sci. USA* 97:6658-6663; Landry et al. (2000) *Biochem. Biophys. Res. Comm.* 278:685-690; Tanner et al. (2000) *Proc. Natl. Acad. Sci. USA* 97:14178-14182; Finnin et al. (2001) *Nat. Struct. Biol.* 8:621-625; MacRae (1997) *Eur. J. Biochem.* 244:265-278; North et al. (2003) *Mol. Cell.* 11:437-444.

SUMMARY OF THE INVENTION

The present invention provides methods for identifying agents that modulate a level or an activity of tubulin deacetylase polypeptide, as well as agents identified by the methods. The invention further provides methods of modulating tubulin deacetylase activity in a cell. The invention further provides methods of modulating cellular proliferation by modulating the activity of tubulin deacetylase.

FEATURES OF THE INVENTION

The invention features an in vitro method of identifying an agent that modulates an enzymatic activity of a human tubulin deacetylase, e.g., human SIRT2. The method generally comprises contacting a tubulin deacetylase polypeptide with a test agent in an assay mixture that comprises nicotinamide adenine dinucleotide (NAD) and an acetylated tubulin peptide; and determining the effect, if any, of the test agent on the enzymatic activity of tubulin deacetylase. In some embodiments, the tubulin deacetylase polypeptide comprises an amino acid sequence as set forth in SEQ ID NO:02. In some embodiments, the acetylated tubulin peptide comprises the sequence $NH_2$-MPSD(AcK)TIGG-$CO_2$ (SEQ ID NO:08). In some embodiments, the acetylated tubulin peptide contains a $^{14}C$-labeled acetyl group on a lysine corresponding to Lys-40 of native tubulin, and determination of the effect of the agent on the enzyme is by measuring release of the radioactive acetyl group. In some embodiments, the effect of the agent on the activity of the enzyme is by detecting binding of an antibody specific for acetylated tubulin.

The present invention further features an in vitro method for identifying an agent that modulates a level of tubulin deacetylase in a cell. The method generally involves contacting a cell that produces tubulin deacetylase with a test agent; and determining the effect, if any, of the test agent on the level of tubulin deacetylase. In some embodiments, determining the effect of the agent involves determining a level of tubulin deacetylase mRNA in the cell. In other embodiments, determining the effect of the agent involves determining a level of tubulin deacetylase polypeptide in the cell.

The present invention further features a biologically active agent identified by a method according to the invention. The present invention further features a pharmaceutical composition comprising a biologically active agent that reduces a level or an activity of a tubulin deacetylase protein; and a pharmaceutically acceptable excipient. The present invention further features a method of modulating cell proliferation, the method comprising contacting a cell with an agent of the invention.

BRIEF DESCRIPTION OF THE DRAWINGS

FIGS. 1A-D depict NAD-dependent deacetylation of a histone peptide by human SIRT2.

FIGS. 2A-C depict inactivation of SIRT2 histone deacetylase activity by point mutations within the SIRT2 catalytic domain.

FIGS. 4A-D depict the substrate preference for SIRT2.

FIGS. 5A and 5B depict regulation of MIZ-1 sub-cellular distribution by acetylated tubulin.

FIGS. 6A and 6B depict the nucleotide and amino acid sequences, respectively, of human SIRT2 (SEQ ID NOs:01 and 02, respectively).

DEFINITIONS

Figure 3A:
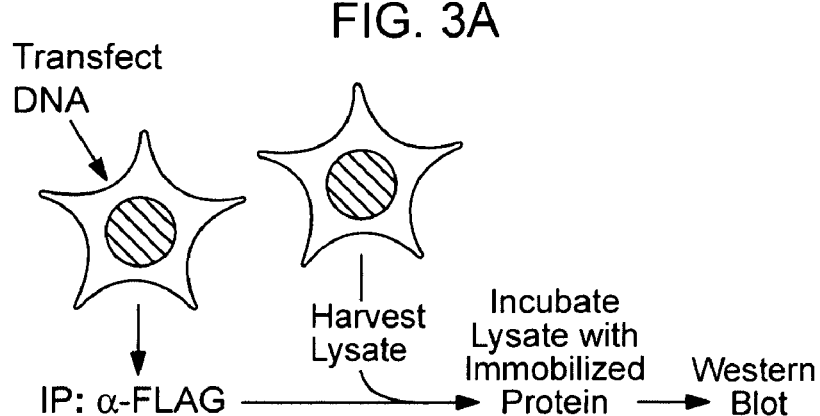
FIGS. 3A-E depict SIRT2 tubulin deacetylates tubulin ex vivo.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "substantially isolated" or "isolated" polypeptide is one that is substantially free of the macromolecules with which it is associated in nature. By substantially free is meant at least 50%, preferably at least 70%, more preferably at least 80%, and even more preferably at least 90% free of the materials with which it is associated in nature.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. Cancerous cells can be benign or malignant.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a tubulin deacetylase" includes a plurality of such deacetylases and reference to "the agent" includes reference to one or more agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of identifying an agent that modulates a level or an activity of tubulin deacetylase; agents identified by the methods; and therapeutic methods, including methods of stabilizing microtubules, methods of controlling unwanted cellular proliferation, and methods of treating disorders associated with or caused by unwanted cellular proliferation.

The invention is based in part on the observation that human SIRT2 is an NAD-dependent tubulin deacetylase. The human SIRT2 enzyme is a cytoplasmic protein that is closely related to the *Saccharomyces cerevisiae* protein Hst2P, which does not deacetylate tubulin; and is an ortholog of the *S. cerevisiae* Silent Information Regulator 2 protein (Sir2p), a histone deacetylase that plays a role in transcriptional silencing. Human SIRT2 removes an acetyl group from lysine-40 of α-tubulin. Deacetylation of tubulin also results in a reduction in the specific interaction of tubulin with the transcription factor myc-interacting zinc finger-1 ("MIZ-1").

Identification of human SIRT2 as a tubulin deacetylase allowed development of assays to identify agents that modulate the activity of this enzyme. Agents that modulate the level or the enzymatic activity of human SIRT2 are useful for modulating cellular proliferation, and are therefore useful, e.g., as anti-cancer agents.

Screening Methods

The invention provides in vitro methods of identifying an agent that modulates a level or an activity of a tubulin deacetylase. The methods generally involve contacting a tubulin deacetylase protein, or a cell that produces a tubulin deacetylase protein, with a test agent, and determining the effect, if any, on a level or an activity of the tubulin deacetylase protein.

In some embodiments, the methods are cell-free methods. Cell-free methods generally involve contacting a tubulin deacetylase with a test agent and determining the effect, if any, of the test agent on the enzymatic activity of the tubulin deacetylase.

In other embodiments, the methods are cell-based methods. Cell-based methods generally involve contacting a cell that produces tubulin deacetylase with a test agent and determining the effect, if any, of the test agent on the level of tubulin deacetylase mRNA or tubulin deacetylase protein in the cell. In some embodiments, cell-based methods involve contacting a cell that produces tubulin deacetylase with a test agent and determining the effect, if any, of the test agent on the binding of a protein to tubulin.

As used herein, the term "determining" refers to both quantitative and qualitative determinations and as such, the term "determining" is used interchangeably herein with "assaying," "measuring," and the like.

The term "tubulin deacetylase polypeptide" encompasses human tubulin deacetylase proteins (e.g., human SIRT2 proteins) having the amino acid sequences set forth in any of GenBank Accession Nos. NM_012237; AF083107; and NM_030593, or depicted in FIG. 6B, where the polypeptide is a cytoplasmic protein and exhibits NAD-dependent tubulin deacetylase activity. The term encompasses variants that have insertions, deletions, and/or conservative amino acid substitutions that do not affect the ability of the protein to deacetylate α-tubulin having an acetylated lysine at position 40. In some embodiments, the tubulin deacetylase is recombinant, e.g., produced in a cell transfected with an expression construct comprising a nucleotide sequence that encodes the tubulin deacetylase.

The term "tubulin deacetylase polypeptide" further encompasses fusion proteins comprising a tubulin deacetylase and a heterologous polypeptide ("fusion partners"), where suitable fusion partners include immunological tags such as epitope tags, including, but not limited to, hemagglutinin, FLAG (see, e.g., Archives of Biochem and Biophys. 406:209-221, 2002; J. Bio. Chem., 277(23):20750-20755, 2002), and the like; proteins that provide for a detectable signal, including, but not limited to, fluorescent proteins (e.g., a green fluorescent protein, a fluorescent protein from an Anthozoan species, and the like), enzymes (e.g., β-galactosidase, luciferase, horse radish peroxidase, etc.), and the like; polypeptides that facilitate purification or isolation of the fusion protein, e.g., metal ion binding polypeptides such as 6H is tags (e.g., tubulin deacetylase/6H is), glutathione-5-transferase (GST), and the like. The term "tubulin deacetylase polypeptide" further includes a tubulin deacetylase polypeptide modified to include one or more specific protease cleavage sites.

Activities attributed to tubulin deacetylase include acetylation of Lys-40 of tubulin; control of MIZ-1/tubulin binding; and the like. Thus, an "activity of tubulin deacetylase" includes direct activity, e.g., acetylation of tubulin; and indirect activities, e.g., a reduction in MIZ-1 binding to tubulin. A MIZ-1 protein amino acid sequence is found under GenBank Accession No. Q13105.

Where the assay is an in vitro cell-free assay, the methods generally involve contacting a tubulin deacetylase polypeptide with a test agent. The tubulin deacetylase polypeptide may be, but need not be, purified. For example, the tubulin deacetylase polypeptide can be in a cell lysate, or may be isolated, or partially purified. Thus, the assay can be conducted in the presence of additional components, as long as the additional components do not adversely affect the reaction to an unacceptable degree.

Where the assay is an in vitro cell-based assay, any of a variety of cells can be used. The cells used in the assay are usually eukaryotic cells, including, but not limited to, rodent cells, human cells, and yeast cells. The cells may be primary cell cultures or may be immortalized cell lines. The cells may be "recombinant," e.g., the cell may have transiently or stably introduced therein a construct (e.g., a plasmid, a recombinant viral vector, or any other suitable vector) that comprises a nucleotide sequence encoding a tubulin deacetylase polypeptide, or that comprises a nucleotide sequence that comprises a tubulin deacetylase promoter operably linked to a reporter gene.

The terms "candidate agent," "test agent," "agent", "substance" and "compound" are used interchangeably herein. Candidate agents encompass numerous chemical classes, typically synthetic, semi-synthetic, or naturally occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.) and can also be used. Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising tubulin deacetylase protein, or a cell that synthesizes tubulin deacetylase) in the absence of the test agent. Generally a plurality of assay mixtures is run in parallel with different agent concentrations to obtain a differential response to the various concentrations. Typically, one of these concentrations serves as a negative control, i.e. at zero concentration or below the level of detection.

Where the screening assay is a binding assay (e.g., binding to tubulin deacetylase; MIZ-1 binding to tubulin), one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

The screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times.

Where the assay is a binding assay, following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound complexes will then be detected.

A test agent of interest is one that reduces a level of tubulin deacetylase protein or inhibits a tubulin deacetylase activity by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the test agent.

Methods of Detecting Agents that Modulate a Level of Tubulin Deacetylase mRNA and/or Tubulin Deacetylase Polypeptide The subject screening methods include methods of detecting an agent that modulates a level of a tubulin deacetylase mRNA and/or tubulin deacetylase polypeptide in a cell. In some embodiments, the methods involve contacting a cell that produces tubulin deacetylase with a test agent, and determining the effect, if any, of the test agent on the level of tubulin deacetylase mRNA in the cell.

A candidate agent is assessed for any cytotoxic activity it may exhibit toward the cell used in the assay, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered candidate agents.

A wide variety of cell-based assays may be used for identifying agents which reduce a level of tubulin deacetylase mRNA in a eukaryotic cell, using, for example, a cell that normally produces tubulin deacetylase mRNA, a mammalian cell transformed with a construct comprising a tubulin deacetylase-encoding cDNA such that the cDNA is overexpressed, or, alternatively, a construct comprising a tubulin deacetylase promoter operably linked to a reporter gene.

Accordingly, the present invention provides a method for identifying an agent, particularly a biologically active agent, that reduces a level of tubulin deacetylase expression in a cell, the method comprising: combining a candidate agent to be tested with a cell comprising a nucleic acid which encodes a tubulin deacetylase polypeptide, or a construct comprising a tubulin deacetylase promoter operably linked to a reporter gene; and determining the effect of said agent on tubulin deacetylase expression. A decrease of at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, in the level (i.e., an amount) of tubulin deacetylase mRNA and/or polypeptide following contacting the cell with a candidate agent being tested, compared to a control to which no agent is added, is an indication that the agent modulates tubulin deacetylase expression.

Tubulin deacetylase mRNA and/or polypeptide whose levels are being measured can be encoded by an endogenous tubulin deacetylase polynucleotide, or the tubulin deacetylase polynucleotide can be one that is comprised within a recombinant vector and introduced into the cell, i.e., the tubulin deacetylase mRNA and/or polypeptide can be encoded by an exogenous tubulin deacetylase polynucleotide. For example, a recombinant vector may comprise an isolated tubulin deacetylase transcriptional regulatory sequence, such as a promoter sequence, operably linked to a reporter gene (e.g., β-galactosidase, chloramphenicol acetyl transferase, a fluorescent protein, luciferase, or other gene that can be easily assayed for expression).

In these embodiments, the method for identifying an agent that modulates a level of tubulin deacetylase expression in a cell, comprises: combining a candidate agent to be tested with a cell comprising a nucleic acid which comprises a tubulin deacetylase gene transcriptional regulatory element operably linked to a reporter gene; and determining the effect of said agent on reporter gene expression. A recombinant vector may comprise an isolated tubulin deacetylase transcriptional regulatory sequence, such as a promoter sequence, operably linked to sequences coding for a tubulin deacetylase polypeptide; or the transcriptional control sequences can be operably linked to coding sequences for a tubulin deacetylase fusion protein comprising tubulin deacetylase polypeptide fused to a polypeptide which facilitates detection. In these embodiments, the method comprises combining a candidate agent to be tested with a cell comprising a nucleic acid which comprises a tubulin deacetylase gene transcriptional regulatory element operably linked to a tubulin deacetylase polypeptide-coding sequence; and determining the effect of said agent on tubulin deacetylase expression, which determination can be carried out by measuring an amount of tubulin deacetylase mRNA, tubulin deacetylase polypeptide, or tubulin deacetylase fusion polypeptide produced by the cell.

Cell-based assays generally comprise the steps of contacting the cell with an agent to be tested, forming a test sample, and, after a suitable time, assessing the effect of the agent on tubulin deacetylase expression. A control sample comprises the same cell without the candidate agent added. Tubulin deacetylase expression levels are measured in both the test sample and the control sample. A comparison is made between tubulin deacetylase expression level in the test sample and the control sample. tubulin deacetylase expression can be assessed using conventional assays. For example, when a mammalian cell line is transformed with a construct that results in expression of tubulin deacetylase, tubulin deacetylase mRNA levels can be detected and measured, or tubulin deacetylase polypeptide levels can be detected and measured. A suitable period of time for contacting the agent with the cell can be determined empirically, and is generally a time sufficient to allow entry of the agent into the cell and to allow the agent to have a measurable effect on tubulin deacetylase mRNA and/or polypeptide levels. Generally, a suitable time is between 10 minutes and 24 hours, or from about 1 hour to about 8 hours.

Methods of measuring tubulin deacetylase mRNA levels are known in the art, several of which have been described above, and any of these methods can be used in the methods of the present invention to identify an agent which modulates tubulin deacetylase mRNA level in a cell, including, but not limited to, a polymerase chain reaction (PCR), such as a PCR employing detectably labeled oligonucleotide primers, and any of a variety of hybridization assays.

Similarly, tubulin deacetylase polypeptide levels can be measured using any standard method, several of which have been described herein, including, but not limited to, an immunoassay such as enzyme-linked immunosorbent assay (ELISA), for example an ELISA employing a detectably labeled antibody specific for a tubulin deacetylase polypeptide.

Tubulin deacetylase polypeptide levels can also be measured in cells harboring a recombinant construct comprising a nucleotide sequence that encodes a tubulin deacetylase fusion protein, where the fusion partner provides for a detectable signal or can otherwise be detected. For example, where the fusion partner provides an immunologically recognizable epitope (an "epitope tag"), an antibody specific for an epitope of the fusion partner can be used to detect and quantitate the level of tubulin deacetylase. In some embodiments, the fusion partner provides for a detectable signal, and in these embodiments, the detection method is chosen based on the type of signal generated by the fusion partner. For example, where the fusion partner is a fluorescent protein, fluorescence is measured.

Fluorescent proteins suitable for use include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria Victoria* or a derivative thereof, e.g., a "humanized" derivative such as Enhanced GFP, which are available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; and the like. Where the fusion partner is an enzyme that yields a detectable product, the product can be detected using an appropriate means, e.g., β-galactosidasecan, depending on the substrate, yield colored product, which is detected spectrophotometrically, or a fluorescent product; luciferase can yield a luminescent product detectable with a luminometer; etc.

A number of methods are available for analyzing nucleic acids for the presence and/or level of a specific mRNA in a cell. The mRNA may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp. 14.2-14.33. Alternatively, various methods are known in the art that utilize oligonucleotide ligation as a means of detecting polymorphisms, for examples see Riley et al. (1990), *Nucl. Acids Res.* 18:2887-2890; and Delahunty et al. (1996), *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, 3S, 3H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

A variety of different methods for determining the nucleic acid abundance in a sample are known to those of skill in the art, where particular methods of interest include those described in: Pietu et al., Genome Res. (June 1996) δ: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

A number of methods are available for determining the expression level of a gene or protein in a particular sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. Alternatively, the secondary antibody conjugated to a fluorescent compound, e.g. fluorescein, rhodamine, Texas red, etc. The absence or presence of antibody binding may be determined by various methods, including flow cytometry of dissociated cells, microscopy, radiography, scintillation counting, etc.

Methods of Detecting Agents that Modulate an Activity of a Tubulin Deacetylase Polypeptide Methods of detecting an agent that modulates an activity of a tubulin deacetylase polypeptide include cell-free and cell-based methods. The methods generally involve contacting a tubulin deacetylase polypeptide with a test agent and determining the effect, if any, on the tubulin deacetylase enzyme activity.

Methods of assaying tubulin deacetylase enzyme activity are known in the art, and any known method can be used. As one non-limiting example, an acetylated tubulin peptide is incubated, together with NAD, with the tubulin deacetylase and a test agent, and the effect, if any, of the test agent on deacetylation of the tubulin peptide is determined. Acetylated tubulin peptides generally comprise an amino acid sequence that comprises the Lys-40 of native tubulin, plus three, four, five, six, seven, or more, amino acids on the $NH_2$ terminal side, and three, four, five, six, seven, or more, amino acids on the $CO_2$ terminal side of the Lys-40 of native tubulin. As one non-limiting example, an acetylated tubulin peptide has the sequence $NH_2$-MPSD(AcK)TIGG-$CO_2$ (SEQ ID NO:08). Those skilled in the art can readily design additional acetylated tubulin peptides. The acetylated tubulin peptide is present in the assay mixture at a concentration of from about 20 μM to about 1 mM, from about 30 μM to about 900 μM, from about 40 μM to about 700 μM, from about 50 μM to about 500 μM, from about 50 μM to about 300 μM, or from about 60 μM to about 100 μM. NAD is present in the assay mixture at a concentration of about 1 mM. The acetyl group on the tubulin peptide is radiolabeled, e.g., $^{14}C$-acetyl is used. The assay then involves determining the amount of $^{14}C$-acetyl that is released, typically by scintillation counting.

Another method of detecting tubulin deacetylase activity is to monitor the acetylation status of tubulin using an antibody specific for acetylated tubulin. Lack of reactivity of the anti-acetylated tubulin antibody with the tubulin substrate indicates that the tubulin has been deacetylated. An example of such an antibody is the 6-11B-1 antibody, as described in the Examples. Thus, in some embodiments, the methods involve determining binding of an anti-acetylated tubulin antibody with the tubulin substrate. Anti-acetylated antibody/tubulin binding can be determined using any type of immunological assay, including immunoblotting assays, ELISA assays, and the like.

In some embodiments, the assay is a cell-free assay, wherein the tubulin deacetylase is contacted with the test agent, the substrate (i.e., acetylated tubulin), and other reaction components (e.g., NAD, buffers, and the like), and the activity of the tubulin deacetylase determined. In these embodiments, the tubulin deacetylase may be purified, but need not be. The tubulin deacetylase may be present in a cell extract; in an immunoprecipitate of a cell extract; or may be partially purified, e.g., at least about 50%, at least about 60%, at least about 70%, at least about 80%, at least about 90%, or more, purified, e.g., free of other macromolecules present in the source of the tubulin deacetylase. The tubulin deacetylase may be recombinant, or may be isolated from a natural source, e.g., a mammalian cell or tissue that normally produced the enzyme.

In other embodiments, the assay is a cell-based in vitro assay, wherein the cell is contacted with the test agent, and the effect, if any, of the agent on the activity of tubulin deacetylase is determined. In these embodiments, the effect of the agent on tubulin deacetylase enzymatic activity is determined by monitoring the acetylation status of tubulin in the cell. The methods involve contacting the cell with the test agent, and, after a suitable period of time, tubulin is extracted from the cell, and the degree of acetylation is determined. The degree of acetylation of tubulin can be determined using any known method, including, e.g., binding of an anti-acetylated tubulin antibody to the tubulin extracted from the cell.

In some embodiments, the assay method involves determining MIZ-1 binding to acetylated tubulin. MIZ-1/tubulin binding can be measured using any known assay, including well-known protein-protein binding assays. Suitable methods include: a yeast two-hybrid method; a fluorescence resonance energy transfer (FRET) assay; a bioluminenscence resonance energy transfer (BRET) assay; a fluorescence quenching assay; a fluorescence anisotropy assay; an immunological assay; and an assay involving binding of a detectably labeled protein to an immobilized protein.

In any assay involving MIZ-1 binding to acetylated tubulin, an acetylated tubulin fragment can be used. Acetylated tubulin fragments are discussed above, and include, but are not limited to, a fragment such as that set forth in SEQ ID NO:08. In any assay involving MIZ-1 binding to acetylated tubulin, MIZ-1 as set forth in SEQ ID NO:09, or an acetylated tubulin-binding fragment of MIZ-1, can be used. In some embodiments, one or both of acetylated tubulin and MIZ-1 protein is detectably labeled.

FRET involves the transfer of energy from a donor fluorophore in an excited state to a nearby acceptor fluorophore. For this transfer to take place, the donor and acceptor molecules must in close proximity (e.g., less than 10 nanometers apart, usually between 10 and 100 Å apart), and the emission spectra of the donor fluorophore must overlap the excitation spectra of the acceptor fluorophore.

In these embodiments, a fluorescently labeled MIZ-1 protein or a tubulin protein serves as a donor and/or acceptor in combination with a second fluorescent protein or dye, e.g., a fluorescent protein as described in Matz et al., Nature Biotechnology (October 1999) 17:969-973; a green fluorescent protein (GFP), including a "humanized" GFP; a GFP from *Aequoria Victoria* or fluorescent mutant thereof, e.g., as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); other fluorescent dyes, e.g., coumarin and its derivatives, e.g. 7-amino-4-methylcoumarin, aminocoumarin, bodipy dyes, such as Bodipy Fla., cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc., chemilumescent dyes, e.g., luciferases.

BRET is a protein-protein interaction assay based on energy transfer from a bioluminescent donor to a fluorescent acceptor protein. The BRET signal is measured by the amount of light emitted by the acceptor to the amount of light emitted by the donor. The ratio of these two values increases as the two proteins are brought into proximity. The BRET assay has been amply described in the literature. See, e.g., U.S. Pat. Nos. 6,020,192; 5,968,750; and 5,874,304; and Xu et al. (1999) *Proc. Natl. Acad. Sci. USA* 96:151-156. BRET assays may be performed by analyzing transfer between a bioluminescent donor protein and a fluorescent acceptor protein. Interaction between the donor and acceptor proteins can be monitored by a change in the ratio of light emitted by the bioluminescent and fluorescent proteins. In this application, the MIZ-1 protein or the tubulin protein serves as donor and/or acceptor protein.

Agents

The present invention further provides biologically active agents identified using a method of the instant invention. A biologically active agent of the invention modulates a level or an activity of a tubulin deacetylase. In some embodiments, an agent that inhibits a tubulin deacetylase is useful in a method of stabilizing tubulin, thereby reducing cell proliferation, and thus is useful to treat cancer.

In many embodiments, the agent is a small molecule, e.g., a small organic or inorganic compound having a molecular weight of more than 50 and less than about 2,500 daltons. Agents may comprise functional groups necessary for structural interaction with proteins, particularly hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof.

In some embodiments, an active agent is a peptide. Suitable peptides include peptides of from about 3 amino acids to about 50, from about 5 to about 30, or from about 10 to about 25 amino acids in length. A peptide of interest inhibits an enzymatic activity of tubulin deacetylase.

Peptides can include naturally-occurring and non-naturally occurring amino acids. Peptides may comprise D-amino acids, a combination of D- and L-amino acids, and various "designer" amino acids (e.g., β-methyl amino acids, Cα-methyl amino acids, and Nα-methyl amino acids, etc.) to convey special properties to peptides. Additionally, peptide may be a cyclic peptide. Peptides may include non-classical amino acids in order to introduce particular conformational motifs. Any known non-classical amino acid can be used. Non-classical amino acids include, but are not limited to, 1,2,3,4-tetrahydroisoquinoline-3-carboxylate; (2S,3S)-methylphenylalanine, (2S,3R)-methyl-phenylalanine, (2R,3S)-methyl-phenylalanine and (2R,3R)-methyl-phenylalanine; 2-aminotetrahydronaphthalene-2-carboxylic acid; hydroxy-1,2,3,4-tetrahydroisoquinoline-3-carboxylate; β-carboline (D and L); HIC (histidine isoquinoline carboxylic acid); and HIC (histidine cyclic urea). Amino acid analogs and peptidomimetics may be incorporated into a peptide to induce or favor specific secondary structures, including, but not limited to, LL-Acp (LL-3-amino-2-propenidone-6-carboxylic acid), a β-turn inducing dipeptide analog; β-sheet inducing analogs; β-turn inducing analogs; α-helix inducing analogs; γ-turn inducing analogs; Gly-Ala turn analog; amide bond isostere; tretrazol; and the like.

A peptide may be a depsipeptide, which may be a linear or a cyclic depsipeptide. Kuisle et al. (1999) *Tet. Letters* 40:1203-1206. "Depsipeptides" are compounds containing a sequence of at least two alpha-amino acids and at least one alpha-hydroxy carboxylic acid, which are bound through at least one normal peptide link and ester links, derived from the hydroxy carboxylic acids, where "linear depsipeptides" may comprise rings formed through S—S bridges, or through an hydroxy or a mercapto group of an hydroxy-, or mercapto-amino acid and the carboxyl group of another amino- or hydroxy-acid but do not comprise rings formed only through peptide or ester links derived from hydroxy carboxylic acids. "Cyclic depsipeptides" are peptides containing at least one ring formed only through peptide or ester links, derived from hydroxy carboxylic acids.

Peptides may be cyclic or bicyclic. For example, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Methods for making cyclic peptides are well known in the art The term "bicyclic" refers to a peptide in which there exists two ring closures. The ring closures are formed by covalent linkages between amino acids in the peptide. A covalent linkage between two nonadjacent amino acids constitutes a ring closure, as does a second covalent linkage between a pair of adjacent amino acids which are already linked by a covalent peptide linkage. The covalent linkages forming the ring closures may be amide linkages, i.e., the linkage formed between a free amino on one amino acid and a free carboxyl of a second amino acid, or linkages formed between the side chains or "R" groups of amino acids in the peptides. Thus, bicyclic peptides may be "true" bicyclic peptides, i.e., peptides cyclized by the formation of a peptide bond between the N-terminus and the C-terminus of the peptide, or they may be "depsi-bicyclic" peptides, i.e., peptides in which the terminal amino acids are covalently linked through their side chain moieties.

A desamino or descarboxy residue can be incorporated at the terminii of the peptide, so that there is no terminal amino or carboxyl group, to decrease susceptibility to proteases or to restrict the conformation of the peptide. C-terminal functional groups include amide, amide lower alkyl, amide di(lower alkyl), lower alkoxy, hydroxy, and carboxy, and the lower ester derivatives thereof, and the pharmaceutically acceptable salts thereof.

In addition to the foregoing N-terminal and C-terminal modifications, a peptide or peptidomimetic can be modified with or covalently coupled to one or more of a variety of hydrophilic polymers to increase solubility and circulation half-life of the peptide. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in Zallipsky, S., Bioconjugate Chem., 6:150-165 (1995); Monfardini, C, et al., Bioconjugate Chem., 6:62-69 (1995); U.S. Pat. Nos. 4,640,835; 4,496,689; 4,301,144; 4,670,417; 4,791,192; 4,179,337 or WO 95/34326.

Another suitable agent for reducing an activity of a tubulin deacetylase is a peptide aptamer. Peptide aptamers are peptides or small polypeptides that act as dominant inhibitors of protein function. Peptide aptamers specifically bind to target proteins, blocking their function ability. Kolonin and Finley, PNAS (1998) 95:14266-14271. Due to the highly selective nature of peptide aptamers, they may be used not only to target a specific protein, but also to target specific functions of a given protein (e.g. a signaling function). Further, peptide aptamers may be expressed in a controlled fashion by use of promoters which regulate expression in a temporal, spatial or inducible manner. Peptide aptamers act dominantly; therefore, they can be used to analyze proteins for which loss-of-function mutants are not available.

Peptide aptamers that bind with high affinity and specificity to a target protein may be isolated by a variety of techniques known in the art. Peptide aptamers can be isolated from random peptide libraries by yeast two-hybrid screens (Xu et al., PNAS (1997) 94:12473-12478). They can also be isolated from phage libraries (Hoogenboom et al., Immunotechnology (1998) 4:1-20) or chemically generated peptides/libraries.

Intracellularly expressed antibodies, or intrabodies, are single-chain antibody molecules designed to specifically bind and inactivate target molecules inside cells. Intrabodies have been used in cell assays and in whole organisms. Chen et al., Hum. Gen. Ther. (1994) 5:595-601; Hassanzadeh et al., Febs Lett. (1998) 16(1, 2):75-80 and 81-86. Inducible expression vectors can be constructed with intrabodies that react specifically with tubulin deacetylase protein. These vectors can be introduced into model organisms and studied in the same manner as described above for aptamers.

In some of the invention, the active agent is an agent that modulates, and generally decreases or down regulates, the expression of the gene encoding tubulin deacetylase in the host. Such agents include, but are not limited to, antisense RNA, interfering RNA, ribozymes, and the like.

In some embodiments, the active agent is an interfering RNA (RNAi). RNAi includes double-stranded RNA interference (dsRNAi). Use of RNAi to reduce a level of a particular mRNA and/or protein is based on the interfering properties of double-stranded RNA derived from the coding regions of gene. In one example of this method, complementary sense and antisense RNAs derived from a substantial portion of the tubulin deacetylase gene are synthesized in vitro. The resulting sense and antisense RNAs are annealed in an injection buffer, and the double-stranded RNA injected or otherwise introduced into the subject (such as in their food or by soaking in the buffer containing the RNA). See, e.g., WO99/32619. In another embodiment, dsRNA derived from a tubulin deacetylase gene is generated in vivo by simultaneous expression of both sense and antisense RNA from appropriately positioned promoters operably linked to tubulin deacetylase coding sequences in both sense and antisense orientations.

Antisense molecules can be used to down-regulate expression of the gene encoding tubulin deacetylase in cells. Antisense compounds include ribozymes, external guide sequence (EGS) oligonucleotides (oligozymes), and other short catalytic RNAs or catalytic oligonucleotides which hybridize to the target nucleic acid and modulate its expression.

The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844). Because the nucleotide sequence of the gene encoding human tubulin deacetylase is known (see, e.g., GenBank Accession No. NT_011109; and GenBank Accession Nos. NM_030593, NM_012237, AJ505014, and AF083107), those skilled in the art can readily generate antisense nucleic acids that reduce the level of a human tubulin deacetylase gene product in a cell.

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which modifications alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-$CH_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The β-anomer of deoxyribose may be used, where the base is inverted with respect to the natural α-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Exemplary modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Oligonucleotides having a morpholino backbone structure (Summerton, J. E. and Weller D. D., U.S. Pat. No. 5,034,506) or a peptide nucleic acid (PNA) backbone (P. E. Nielson, M. Egholm, R. H. Berg, O. Buchardt, Science 1991, 254: 1497) can also be used. Morpholino antisense oligonucleotides are amply described in the literature. See, e.g., Partridge et al. (1996) *Antisense Nucl. Acid Drug Dev.* 6:169-175; and Summerton (1999) *Biochem. Biophys. Acta* 1489:141-158.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43-56.

Formulations, Dosages, and Routes of Administration

The invention provides formulations, including pharmaceutical formulations, comprising an agent that reduces a level and/or an activity of tubulin deacetylase. In general, a formulation comprises an effective amount of an agent that reduces a level and/or an activity of tubulin deacetylase. An "effective amount" means a dosage sufficient to produce a desired result, e.g., a reduction in a level and/or an activity of tubulin deacetylase, stabilization of microtubules; a reduction in tubulin deacetylation; a reduction in cell proliferation; and the like. Generally, the desired result is at least a reduction a level and/or an activity of tubulin deacetylase as compared to a control.

Formulations

In the subject methods, the active agent(s) may be administered to the host using any convenient means capable of resulting in the desired reduction in a level and/or an activity of tubulin deacetylase. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 μg to about 1,000 μg or about 10,000 μg of an agent that reduces a level and/or an activity of tubulin deacetylase can be administered in a single dose. Alternatively, a target dosage of an agent that reduces a level and/or an activity of tubulin deacetylase can be considered to be about in the range of about 0.1-1000 μM, about 0.5-500 μM, about 1-100 μM, or about 5-50 μM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that reduces a level and/or an activity of tubulin deacetylase is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an allergic hypersensitivity. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Combination Therapies

The present invention also provides methods of treating cancer, and methods of reducing unwanted cellular proliferation, involving administering an agent that modulates (e.g., inhibits) a tubulin deacetylase; and a second therapeutic agent. In some embodiments, an agent that inhibits a tubulin deacetylase is administered as an adjuvant to a standard cancer therapy.

Standard cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indoledionones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use in connection with the methods of the invention include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ (8) colony-stimulating factors; (9) inhibitors of angiogenesis; and (10) antagonists of tumor necrosis factor.

Therapeutic Methods

The present invention provides methods of modulating tubulin acetylation; methods of stabilizing microtubules; methods of reducing unwanted cellular proliferation; and methods of treating disorders resulting from unwanted cellular proliferation. The methods generally involve administering to an individual an effective amount of a subject agent that modulates (e.g., inhibits) an enzymatic activity of tubulin deacetylase (e.g., SIRT2), in an amount effective to reduce unwanted cellular proliferation. An effective amount of a subject agent reduces cell proliferation, and/or decreases tumor mass.

An agent that inhibits tubulin deacetylase enzymatic activity is administered to a patient in need thereof, e.g., a patient who has cancer.

In the context of reducing unwanted cell proliferation, and reducing tumor mass, an effective amount of an agent that inhibits tubulin deacetylase is an amount that reduces the level and/or rate of cell proliferation and/or reduces tumor mass by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 85%, or at least about 90%, or more, compared to the level and/or rate of cell proliferation and/or tumor mass in the absence of treatment with an agent that inhibits tubulin deacetylase.

Whether a particular agent reduces the rate and/or level of cell proliferation can be determined using any known assay. For example, an in vitro assay can be used, in which cells (e.g., tumor cells) are cultured in culture medium to which has been added an agent. Cell proliferation is determined using any known assay, e.g., $^3$H-thymidine incorporation; counting viable cell number. Viable cell number can be counted using any known method. For example, a fluorescence activated cell sorting (FACS) method is used to determine the number of cells that are stained with a viable cell stain (e.g., fluorescein di-O-acetate, and the like), compared to the number of cells stained with a dye that does not normally stain viable cells, such as propidium iodide.

Whether a particular therapeutic regimen of the invention is effective in reducing unwanted cellular proliferation, e.g., in the context of treating cancer, can be determined using standard methods. For example, the number of cancer cells in a biological sample (e.g., blood, a biopsy sample, and the like), can be determined. The tumor mass can be determined using standard radiological methods.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen) to determine the number of cells bearing a given tumor antigen; computed tomography scanning, magnetic resonance imaging, and/or x-ray imaging of the tumor to estimate and/or monitor tumor size; measuring the amount of tumor-associated antigen in a biological sample, e.g., blood, serum, etc.; and the like.

Whether growth of a tumor is inhibited can be determined using any known method, including, but not limited to, an in vitro cell proliferation assay (e.g., counting cell number); a $^3$H-thymidine uptake assay; and the like.

An agent that inhibits tubulin deacetylase is administered by any route of administration. Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect.

The agent can be administered in a single dose or in multiple doses. For example, an agent that inhibits tubulin deacetylase is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

In some embodiments, an agent that inhibits a tubulin deacetylase is administered as an adjuvant to a standard cancer therapy, as described above.

In some embodiments, the methods involve administering an effective amount of an agent that inhibits tubulin deacetylase, and co-administering to the cancer patient an effective amount of at least one additional antineoplastic drug that is an alkylating agent. In some embodiments, the alkylating agent is a nitrogen mustard. In other embodiments, the alkylating agent is an ethylenimine. In still other embodiments, the alkylating agent is an alkylsulfonate. In additional embodiments, the alkylating agent is a triazene. In further embodiments, the allylating agent is a nitrosourea.

In some embodiments, the methods involve administering an effective amount of an agent that inhibits tubulin deacetylase, and co-administering to the cancer patient an effective amount of at least one additional antineoplastic drug that is an antimetabolite. In some embodiments, the antimetabolite is a folic acid analog, such as methotrexate. In other embodiments, the antimetabolite is a purine analog, such as mercaptopurine, thioguanine and axathioprine. In still other embodiments, the antimetabolite is a pyrimidine analog, such as 5FU, UFT, capecitabine, gemcitabine and cytarabine.

In some embodiments, the methods involve administering an effective amount of an agent that inhibits tubulin deacetylase, and co-administering to the cancer patient an effective amount of at least one additional antineoplastic drug that is a vinca alkyloid. In some embodiments, the vinca alkaloid is a taxane, such as paclitaxel. In other embodiments, the vinca alkaloid is a podophyllotoxin, such as etoposide, teniposide, ironotecan, and topotecan.

In some embodiments, the methods involve administering an effective amount of an agent that inhibits tubulin deacetylase, and co-administering to the cancer patient an effective amount of at least one additional antineoplastic drug that is an antineoplastic antibiotic. In some embodiments, the antineoplastic antibiotic is doxorubicin.

In some embodiments, the methods involve administering an effective amount of an agent that inhibits tubulin deacetylase, and co-administering to the cancer patient an effective amount of at least one additional antineoplastic drug that is a platinum complex. In some embodiments, the platinum complex is cisplatin. In other embodiments, the platinum complex is carboplatin.

In some embodiments, the methods involve administering an effective amount of an agent that inhibits tubulin deacetylase, and co-administering to the cancer patient an effective amount of at least one additional antineoplastic drug that is a tyrosine kinase inhibitor. In some embodiments, the tyrosine kinase inhibitor is a receptor tyrosine kinase (RTK) inhibitor, such as type I receptor tyrosine kinase inhibitors (e.g., inhibitors of epidermal growth factor receptors), type II receptor tyrosine kinase inhibitors (e.g., inhibitors of insulin receptor), type III receptor tyrosine kinase inhibitors (e.g., inhibitors of platelet-derived growth factor receptor), and type IV receptor tyrosine kinase inhibitors (e.g., fibroblast growth factor receptor). In other embodiments, the tyrosine kinase inhibitor is a non-receptor tyrosine kinase inhibitor, such as inhibitors of src kinases or janus kinases.

In some embodiments, the methods involve administering an effective amount of an agent that inhibits tubulin deacetylase, and co-administering to the cancer patient an effective amount of at least one additional antineoplastic drug that is an inhibitor of a receptor tyrosine kinase involved in growth factor signaling pathway(s). In some embodiments, the inhibitor is genistein. In other embodiments, the inhibitor is an epidermal growth factor receptor (EGFR) tyrosine kinase-specific antagonist, such as IRESSA™ gefitinib, TARCEVA™ erolotinib, or tyrphostin AG1478 (4-(3-chloroanilino)-6,7-dimethoxyquinazoline. In still other embodiments, the inhibitor is any indolinone antagonist of Flk-1/KDR (VEGF-R2) tyrosine kinase activity. In further embodiments, the inhibitor is any of the substituted 3-[(4,5,6,7-tetrahydro-1H-indol-2-yl)methylene]-1,3-dihydroindol-2-one antagonist of Flk-1/KDR (VEGF-R2), FGF-R1 or PDGF-R tyrosine kinase activity. In additional embodiments, the inhibitor is any substituted 3-[(3- or 4-carboxyethylpyrrol-2-yl)methylidenyl]indolin-2-one antagonist of Flt-1 (VEGF-R1), Flk-1/KDR (VEGF-R2), FGF-R1 or PDGF-R tyrosine kinase activity.

In some embodiments, the methods involve administering an effective amount of an agent that inhibits tubulin deacetylase, and co-administering to the cancer patient an effective amount of at least one additional antineoplastic drug that is an inhibitor of a non-receptor tyrosine kinase involved in growth factor signaling pathway(s). In some embodiments, the inhibitor is an antagonist of JAK2 tyrosine kinase activity, such as tyrphostin AG490 (2-cyano-3-(3,4-dihydroxyphenyl)-N-(benzyl)-2-propenamide). In other embodiments, the inhibitor is an antagonist of bcr-abl tyrosine kinase activity, such as GLEEVEC™ imatinib mesylate.

In some embodiments, the methods involve administering an effective amount of an agent that inhibits tubulin deacetylase, and co-administering to the cancer patient an effective amount of at least one additional antineoplastic drug that is a serine/threonine kinase inhibitor. In some embodiments, the serine/threonine kinase inhibitor is a receptor serine/threonine kinase inhibitor, such as antagonists of TGF-β receptor serine/threonine kinase activity. In other embodiments, the serine/threonine kinase inhibitor is a non-receptor serine/threonine kinase inhibitor, such as antagonists of the serine/threonine kinase activity of the MAP kinases, protein kinase C(PKC), protein kinase A (PKA), or the cyclin-dependent kinases (CDKs).

In some embodiments, the methods involve administering an effective amount of an agent that inhibits tubulin deacetylase, and co-administering to the cancer patient an effective amount of at least one additional antineoplastic drug that is an inhibitor of one or more kinases involved in cell cycle regulation. In some embodiments, the inhibitor is an antagonist of CDK2 activation, such as tryphostin AG490 (2-cyano-3-(3,4-dihydroxyphenyl)-N-(benzyl)-2-propenamide). In other embodiments, the inhibitor is an antagonist of CDK1/cyclin B activity, such as alsterpaullone. In still other embodiments, the inhibitor is the antagonist of CDK2 kinase activity, such as indirubin-3'-monoxime.

In some embodiments, the methods involve administering an effective amount of an agent that inhibits tubulin deacetylase, and co-administering to the patient an effective amount of a taxane. In some embodiments, the methods involve administering an effective amount of an agent that inhibits tubulin deacetylase, and co-administering to the patient an effective amount of a taxane, and an effective amount of a platinum complex. In some embodiments, the taxane is paclitaxel and the platinum complex is cisplatin or carboplatin.

In some embodiments, the methods involve administering an effective amount of an agent that inhibits tubulin deacetylase, and co-administering to the patient an effective amount of at least one additional antineoplastic drug that is an a tumor-associated antigen antagonist, such as an antibody antagonist. In some embodiments involving the treatment of HER2-expressing tumors, the tumor-associated antigen antagonist is an anti-HER2 monoclonal antibody, such as HERCEPTIN™ trastuzumab. In some embodiments involving the treatment of CD20-expressing tumors, such as B-cell lymphomas, the tumor-associated antigen antagonist is an anti-CD20 monoclonal antibody, such as RITUXAN™ rituximab.

In some embodiments, the methods involve administering an effective amount of an agent that inhibits tubulin deacetylase, and co-administering to the patient an effective amount of at least one additional antineoplastic drug that is a tumor growth factor antagonist. In some embodiments, the tumor growth factor antagonist is an antagonist of epidermal growth factor (EGF), such as an anti-EGF monoclonal antibody. In other embodiments, the tumor growth factor antagonist is an antagonist of epidermal growth factor receptor erbB1 (EGFR), such as an anti-EGFR monoclonal antibody antagonist of EGFR activation or signal transduction.

In some embodiments, the agent that inhibits tubulin deacetylase is ribavirin or a ribavirin derivative. Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. The invention also contemplates use of derivatives of ribavirin (see, e.g., U.S. Pat. No. 6,277,830). The ribavirin may be administered orally in capsule or tablet form. Of course, other types of administration, as they become available are contemplated, such as by nasal spray, transdermally, intravenously, by suppository, by sustained release dosage form, etc. Any form of administration will work so long as the proper dosages are delivered without destroying the active ingredient.

Ribavirin is generally administered in an amount ranging from about 30 mg to about 1200 mg per day, e.g., from about 30 mg to about 60 mg, from about 60 mg to about 125 mg, from about 125 mg to about 200 mg, from about 200 mg to about 300 mg, from about 300 mg to about 400 mg, from about 400 mg to about 600 mg, from about 600 mg to about 800 mg, from about 800 mg to about 1000 mg, or from about 1000 mg to about 1200 mg per day.

Exemplary non-limiting examples of combination therapies that include treatment with radiation, tubulin deacetylase inhibiting agent, or treatment with a chemotherapeutic agent and tubulin deacetylase inhibiting agent, are as follows:

1) a dosage of an agent that inhibits tubulin deacetylase; and cisplatin in a dosage range of from about 5 mg/m$^2$ to about 150 mg/m$^2$;

2) a dosage of an agent that inhibits tubulin deacetylase; and carboplatin in a dosage range of from about 5 mg/m$^2$ to about 1000 mg/m$^2$;

3) a dosage of an agent that inhibits tubulin deacetylase; and radiation in a dosage range of from about 200 cGy to about 8000 cGy;

4) a dosage of an agent that inhibits tubulin deacetylase; and paclitaxel in a dosage range of from about 40 mg/m$^2$ to about 250 mg/m$^2$;

5) a dosage of an agent that inhibits tubulin deacetylase; paclitaxel in a dosage range of from about 40 mg/m$^2$ to about 250 mg/m$^2$; and carboplatin in a dosage range of from about 5 mg/m$^2$ to about 1000 mg/m$^2$;

6) a dosage of an agent that inhibits tubulin deacetylase; 5FU in a dosage range of from about 5 mg/m$^2$ to about 5000 mg/m$^2$; and leucovorin in a dosage range of from about 5 mg/m$^2$ to about 1000 mg/m$^2$;

7) a dosage of an agent that inhibits tubulin deacetylase; and trastuzumab in an initial loading dose of 4 mg/kg and a weekly maintenance dose of 2 mg/kg;

8) a dosage of an agent that inhibits tubulin deacetylase; trastuzumab in an initial loading dose of 4 mg/kg and a weekly maintenance dose of 2 mg/kg; and paclitaxel in a dosage range of from about 40 mg/m$^2$ to about 250 mg/m$^2$;

9) a dosage of an agent that inhibits tubulin deacetylase; paclitaxel in a dosage range of from about 40 mg/m$^2$ to about 250 mg/m$^2$; and estramustine phosphate (Emcyte®) in a dosage range of from about 5 mg/m$^2$ to about 1000 mg/m$^2$;

10) a dosage of an agent that inhibits tubulin deacetylase; cisplatin in a dosage range of from about 5 mg/m$^2$ to about 150 mg/m$^2$; and 5FU in a dosage range of from about 5 mg/m$^2$ to about 5000 mg/m$^2$.

11) dosage of an agent that inhibits tubulin deacetylase; 5FU in a dosage range of from about 5 mg/m$^2$ to about 5000 mg/m$^2$; and radiation in a dose of from about 200 cGy to about 8000 cGy; and 12) dosage of an agent that inhibits tubulin deacetylase; 5FU in a dosage range of from about 5 mg/m$^2$ to about 5000 mg/m$^2$; and paclitaxel in a dosage range of from about 40 mg/m$^2$ to about 250 mg/m$^2$.

In any of examples 1-12 of combination therapies discussed above, ribavirin in a dose of from about 30 to about 1200 mg/day can be administered to the patient orally.

Subject Suitable for Treatment

An agent that reduces a level of a tubulin deacetylase and/or that inhibits a tubulin deacetylase enzymatic activity is useful for treating cancer in a patient having a cancer. The methods are useful for treating a wide variety of cancers, including carcinomas, sarcomas, leukemias, and lymphomas. A patient having any cancer is suitable for treatment with a subject method.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; and the like.

REFERENCES

1. Abraham, J., Kelly, J., Thibault, P., and Benchimol, S. (2000). Post-translational modification of p53 protein in response to ionizing radiation analyzed by mass spectrometry. Journal of Molecular Biology 295, 853-64.
2. Afshar, G. and Murnane, J. P. (1999). Characterization of a human gene with sequence homology to *Saccharomyces cerevisiae* SIR2. Gene 234, 161-8.
3. Brachmann, C. B., Sherman, J. M., Devine, S. E., Cameron, E. E., Pillus, L., and Boeke, J. D. (1995). The SIR2 gene family, conserved from bacteria to humans, functions in silencing, cell cycle progression, and chromosome stability. Genes and Development 9, 2888-902.
4. Chen, L., Fischle, W., Verdin, E., and Greene, W. C. (2001). Duration of nuclear NF-kappaB action regulated by reversible acetylation. Science 293, 1653-7.
5. Defossez, P. A., Park, P. U., and Guarente, L. (1998). Vicious circles: a mechanism for yeast aging. Curr Opin Microbiol 1, 707-11.
6. Dignam, J. D., Lebovitz, R. M., and Roeder, R. G. (1983). Accurate transcription initiation by RNA polymerase II in a soluble extract from isolated mammalian nuclei. Nucleic Acids Res 11, 1475-89.
7. Elliott, G. and O'Hare, P. (1998). Herpes simplex virus type 1 tegument protein VP22 induces the stabilization and hyperacetylation of microtubules. Journal of Virology 72, 6448-55.
8. Emiliani, S., Fischle, W., Van Lint, C., Al-Abed, Y., and Verdin, E. (1998). Characterization of a human RPD3 ortholog, HDAC3. Proc Natl Acad Sci USA 95, 2795-800.
9. Finnin, M. S., Donigian, J. R., and Pavletich, N. P. (2001). Structure of the histone deacetylase SIRT2. Nat Struct Biol 8, 621-5.
10. Fischle, W., Kiermer, V., Dequiedt, F., and Verdin, E. (2001). The emerging role of class II histone deacetylases. Biochem Cell Biol 79, 337-48.

11. Frye, R. A. (1999). Characterization of five human cDNAs with homology to the yeast SIR2 gene: Sir2-like proteins (sirtuins) metabolize NAD and may have protein ADP-ribosyltransferase activity. Biochemical and Biophysical Research Communications 260, 273-9.
12. Frye, R. A. (2000). Phylogenetic classification of prokaryotic and eukaryotic Sir2-like proteins. Biochemical and Biophysical Research Communications 273, 793-8.
13. Furumai, R., Komatsu, Y., Nishino, N., Khochbin, S., Yoshida, M., and Horinouchi, S. (2001). Potent histone deacetylase inhibitors built from trichostatin A and cyclic tetrapeptide antibiotics including trapoxin. Proc Natl Acad Sci USA 98, 87-92.
14. Grozinger, C. M., Chao, E. D., Blackwell, H. E., Moazed, D., and Schreiber, S. L. (2001). Identification of a class of small molecule inhibitors of the sirtuin family of NAD-dependent deacetylases by phenotypic screening. J Biol Chem 276, 38837-43.
15. Gu, W. and Roeder, R. G. (1997). Activation of p53 sequence-specific DNA binding by acetylation of the p53 C-terminal domain. Cell 90, 595-606.
16. Harrison, R. E. and Turley, E. A. (2001). Active erk regulates microtubule stability in H-ras-transformed cells. Neoplasia 3, 385-94.
17. Hecht, A., Laroche, T., Strahl-Bolsinger, S., Gasser, S. M., and Grunstein, M. (1995). Histone H3 and $H_4$N-termini interact with SIR3 and SIR4 proteins: a molecular model for the formation of heterochromatin in yeast. Cell 80, 583-92.
18. Hu, E., Chen, Z., Fredrickson, T., Zhu, Y., Kirkpatrick, R., Zhang, G. F., Johanson, K., Sung, C. M., Liu, R., and Winkler, J. (2000). Cloning and characterization of a novel human class I histone deacetylase that functions as a transcription repressor. J Biol Chem 275, 15254-64.
19. Imai, S., Armstrong, C. M., Kaeberlein, M., and Guarente, L. (2000). Transcriptional silencing and longevity protein Sir2 is an NAD-dependent histone deacetylase. Nature 403, 795-800.
20. Jenuwein, T. and Allis, C. D. (2001). Translating the histone code. Science 293, 1074-80.
21. Kao, H. Y., Lee, C. H., Komarov, A., Han, C. C., and Evans, R. M. (2002). Isolation and characterization of mammalian HDAC10, a novel histone deacetylase. J Biol Chem 277, 187-93.
22. Kuo, M. H. and Allis, C. D. (1998). Roles of histone acetyltransferases and deacetylases in gene regulation. Bioessays 20, 615-26.
23. Landry, J., Sutton, A., Tafrov, S. T., Heller, R. C., Stebbins, J., Pillus, L., and Sternglanz, R. (2000). The silencing protein SIR2 and its homologs are NAD-dependent protein deacetylases. Proceedings of the National Academy of Sciences of the United States of America 97, 5807-11.
24. Luo, J., Nikolaev, A. Y., Imai, S., Chen, D., Su, F., Shiloh, A., Guarente, L., and Gu, W. (2001). Negative Control of p53 by Sir2alpha Promotes Cell Survival under Stress. Cell 107, 137-148.
25. MacRae, T. H. (1997). Tubulin post-translational modifications—enzymes and their mechanisms of action. European Journal of Biochemistry 244, 265-78.
26. Martin, S. G., Laroche, T., Suka, N., Grunstein, M., and Gasser, S. M. (1999). Relocalization of telomeric Ku and SIR proteins in response to DNA strand breaks in yeast. Cell 97, 621-33.
27. Martinez-Balbás, M. A., Bauer, U. M., Nielsen, S. J., Brehm, A., and Kouzarides, T. (2000). Regulation of E2F1 activity by acetylation. Embo Journal 19, 662-71.
28. Mattaj, I. W. and Englmeier, L. (1998). Nucleocytoplasmic transport: the soluble phase. Annu Rev Biochem 67, 265-306.
29. McAinsh, A. D., Scott-Drew, S., Murray, J. A., and Jackson, S. P. (1999). DNA damage triggers disruption of telomeric silencing and Mec1p-dependent relocation of Sir3p. Current Biology 9, 963-6.
30. Mills, K. D., Sinclair, D. A., and Guarente, L. (1999). MEC 1-dependent redistribution of the Sir3 silencing protein from telomeres to DNA double-strand breaks. Cell 97, 609-20.
31. Moretti, P., Freeman, K., Coodly, L., and Shore, D. (1994). Evidence that a complex of SIR proteins interacts with the silencer and telomere-binding protein RAP1. Genes and Development 8, 2257-69.
32. Munshi, N., Agalioti, T., Lomvardas, S., Merika, M., Chen, G., and Thanos, D. (2001). Coordination of a transcriptional switch by HMGI(Y) acetylation. [Comment In: Science. 2001 Aug. 10; 293(5532):1054-5 UI: 21390028]. Science 293, 1133-6.
33. Nogales, E. (2000). Structural insights into microtubule function. Annual Review of Biochemistry 69, 277-302.
34. Nogales, E., Whittaker, M., Milligan, R. A., and Downing, K. H. (1999). High-resolution model of the microtubule. Cell 96, 79-88.
35. Nogales, E., Wolf, S. G., and Downing, K. H. (1998). Structure of the alpha beta tubulin dimer by electron crystallography. Nature 391, 199-203.
36. Ott, M., Schnolzer, M., Garnica, J., Fischle, W., Emiliani, S., Rackwitz, H. R., and Verdin, E. (1999). Acetylation of the HIV-1 Tat protein by p300 is important for its transcriptional activity. Curr Biol 9, 1489-92.
37. Perrod, S., Cockell, M. M., Laroche, T., Renauld, H., Ducrest, A. L., Bonnard, C., and Gasser, S. M. (2001). A cytosolic NAD-dependent deacetylase, Hst2p, can modulate nucleolar and telomeric silencing in yeast. Embo Journal 20, 197-209.
38. Pijnappel, W. W., Schaft, D., Roguev, A., Shevchenko, A., Tekotte, H., Wilm, M., Rigaut, G., Seraphin, B., Aasland, R., and Stewart, A. F. (2001). The *S. cerevisiae* SET3 complex includes two histone deacetylases, Hos2 and Hst1, and is a meiotic-specific repressor of the sporulation gene program. Genes Dev 15, 2991-3004.
39. Piperno, G., LeDizet, M., and Chang, X. J. (1987). Microtubules containing acetylated alpha-tubulin in mammalian cells in culture. Journal of Cell Biology 104, 289-302.
40. Poole, C. A., Zhang, Z. J., and Ross, J. M. (2001). The differential distribution of acetylated and detyrosinated alpha-tubulin in the microtubular cytoskeleton and primary cilia of hyaline cartilage chondrocytes. J Anat 199, 393-405.
41. Rine, J. and Herskowitz, I. (1987). Four genes responsible for a position effect on expression from HML and HMR in *Saccharomyces cerevisiae*. Genetics 116, 9-22.
42. Rine, J., Strathern, J. N., Hicks, J. B., and Herskowitz, I. (1979). A suppressor of mating-type locus mutations in *Saccharomyces cerevisiae*: evidence for and identification of cryptic mating-type loci. Genetics 93, 877-901.
43. Sakaguchi, K., Herrera, J. E., Saito, S., Miki, T., Bustin, M., Vassilev, A., Anderson, C. W., and Appella, E. (1998). DNA damage activates p53 through a phosphorylation-acetylation cascade. Genes and Development 12, 2831-41.
44. Saragoni, L., Hernandez, P., and Maccioni, R. B. (2000). Differential association of tau with subsets of microtubules containing posttranslationally-modified tubulin variants in neuroblastoma cells. Neurochem Res 25, 59-70.

45. Shore, D., Squire, M., and Nasmyth, K. A. (1984). Characterization of two genes required for the position-effect control of yeast mating-type genes. Embo Journal 3, 2817-23.
46. Shou, W., Seol, J. H., Shevchenko, A., Baskerville, C., Moazed, D., Chen, Z. W., Jang, J., Charbonneau, H., and Deshaies, R. J. (1999). Exit from mitosis is triggered by Tem1-dependent release of the protein phosphatase Cdc14 from nucleolar RENT complex. Cell 97, 233-44.
47. Smith, J. S, and Boeke, J. D. (1997). An unusual form of transcriptional silencing in yeast ribosomal DNA. Genes and Development 11, 241-54.
48. Smith, J. S., Brachmann, C. B., Celic, I., Kenna, M. A., Muhammad, S., Starai, V. J., Avalos, J. L., Escalante-Semerena, J. C., Grubmeyer, C., Wolberger, C., and Boeke, J. D. (2000). A phylogenetically conserved NAD+-dependent protein deacetylase activity in the Sir2 protein family. Proceedings of the National Academy of Sciences of the United States of America 97, 6658-63.
49. Sterner, R., Vidali, G., and Allfrey, V. G. (1981). Studies of acetylation and deacetylation in high mobility group proteins. Identification of the sites of acetylation in high mobility group proteins 14 and 17. Journal of Biological Chemistry 256, 8892-5.
50. Strahl-Bolsinger, S., Hecht, A., Luo, K., and Grunstein, M. (1997). SIR2 and SIR4 interactions differ in core and extended telomeric heterochromatin in yeast. Genes and Development 11, 83-93.
51. Straight, A. F., Shou, W., Dowd, G. J., Turck, C. W., Deshaies, R. J., Johnson, A. D., and Moazed, D. (1999). Net1, a Sir2-associated nucleolar protein required for rDNA silencing and nucleolar integrity. Cell 97, 245-56.
52. Takemura, R., Okabe, S., Umeyama, T., Kanai, Y., Cowan, N. J., and Hirokawa, N. (1992). Increased microtubule stability and alpha tubulin acetylation in cells transfected with microtubule-associated proteins MAP1B, MAP2 or tau. Journal of Cell Science 103, 953-64.
53. Tanner, K. G., Landry, J., Sternglanz, R., and Denu, J. M. (2000). Silent information regulator 2 family of NAD-dependent histone/protein deacetylases generates a unique product, 1-O-acetyl-ADP-ribose. [Comment In: Proc Natl Acad Sci USA. 2000 Dec. 19; 97(26):14030-2 UI: 20570422]. Proceedings of the National Academy of Sciences of the United States of America 97, 14178-82.
54. Vaziri, H., Dessain, S. K., Eaton, E. N., Imai, S. I., Frye, R. A., Pandita, T. K., Guarente, L., and Weinberg, R. A. (2001). hSIR2(SIRT1) Functions as an NAD-Dependent p53 Deacetylase. Cell 107, 149-159.
55. Yang, Y. H., Chen, Y. H., Zhang, C. Y., Nimmakayalu, M. A., Ward, D.C., and Weissman, S. (2000). Cloning and characterization of two mouse genes with homology to the yeast Sir2 gene. Genomics 69, 355-69.
56. Yoshida, M., Kijima, M., Akita, M., and Beppu, T. (1990). Potent and specific inhibition of mammalian histone deacetylase both in vivo and in vitro by trichostatin A. J Biol Chem 265, 17174-9.
57. Zhou, X., Marks, P. A., Rifkind, R. A., and Richon, V. M. (2001). Cloning and characterization of a histone deacetylase, HDAC9. Proc Natl Acad Sci USA 98, 10572-7.
58. Ziegelbauer, J., Shan, B., Yager, D., Larabell, C., Hoffmann, B., and Tjian, R. (2001). Transcription factor MIZ-1 is regulated via microtubule association. Mol Cell 8, 339-49.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. Standard abbreviations may be used, e.g., bp, base pair(s); kb, kilobase(s); pl, picoliter(s); s, second(s); min, minute(s); hr, hour(s); and the like.

Example 1

Characterization of Human SIRT2

Experimental Procedures

Tissue Culture

HEK 293T and HeLa were obtained from ATCC, grown in DMEM supplemented with 10% Fetal Bovine Serum (Gemini Bio-products, Woodland, Calif.) in the presence of penicillin, streptomycin and 2 mM L-Glutamine (Gibco Invitrogen Corp., Carlsbad, Calif.). HepG2 was obtained form ATCC and grown in medium as described for above with the addition of 0.1 mM MEM non-essential amino acids (Gibco Invitrogen Corp., Carlsbad, Calif.).

Plasmids and Mutagenesis

For recombinant SIRT2, human SIRT2 cDNA in pHEX (a gift from R. Frye) was altered to insert a factor Xa protease cleavage site. Human SIRT1 and SIRT3 constructs were also a gift from R. Frye. Human SIRT4-7 were cloned from testis and spleen cDNA libraries (Clontech, Mountain View, Calif.) into pcDNA3.1(+) vector by standard of PCR-based strategies and confirmed by sequencing. All SIRT cDNAs were sub-cloned to generate C-terminal FLAG-tagged fusions in the pcDNA3.1 (+) backbone (InVitrogen, Carlsbad, Calif.) and wild type human SIRT2 was cloned into pEGFP-C1 vector (Clontech, Mountain View, Calif.) by standard PCR-based strategies. pEGFP-MIZ-1 was a kind gift from J. E. Wilson. Site directed mutagenesis for SIRT2 constructs were performed using QuikChange Site-Directed Mutagenesis Kit (Stratagene, La Jolla, Calif.) performed as described by manufacturer.

Purification of Recombinant SIRT2

DH5αFIQ bacteria (Gibco Invitrogen Corp., Carlsbad, Calif.) were transformed with pHEX vector containing the human SIRT2 cDNA with factor Xa cleavage site and induced with 0.1 mM IPTG at 37° C. for 2 h. Resultant 6× His-tagged protein was purified under native conditions at 4° C. by Ni-NTA (Qiagen, Valencia, Calif.), HiPrep 26/10 Desalting and Sepharose Q chromatographies (Amersham Pharmacia Biotech, Inc., Piscataway, N.J.). Recombinant protein was aliquoted and stored at −20° C.

Transient Transfections and Immunoprecipitations

HEK 293T cells were transfected by calcium phosphate DNA precipitation method and lysed 48 hours post-transfection in low stringency lysis buffer (50 mM Tris-HCl, pH 7.5, 0.5 mM EDTA, 0.5% NP-40, 150 mM NaCl) in the presence of protease inhibitor cocktail (Complete, Roche Molecular Biochemicals, Indianapolis, Ind.). FLAG tagged proteins were immunoprecipitated with anti-FLAG M2 agarose affinity gel (Sigma, St. Louis, Mo.) and GFP-tagged proteins were immunoprecipitated with anti-GFP monoclonal antibody (Sigma, St. Louis, Mo.) in the presence of Protein G Sepharose (Amersham Pharmacia Biotech, Inc., Piscataway, N.J.) for 2 hours at 4° C. Immunoprecipitated material was washed 3 times in low stringency lysis buffer and one time in SIRT2 deacetylase buffer (50 mM Tris-HCl, pH 9.0, 4 mM $MgCl_2$, and 0.2 mM dithiothreitol (DTT)).

Nuclear and Cytoplasmic Extracts.

HEK 293T cells were transfected as described above and subjected to nuclear and cytoplasmic extraction as described previously (Dignam et al., 1983) modified by the addition of 1.0% NP-40 to buffer C.

Histone Deacetylase Assay

Immunoprecipitated material and recombinant SIRT2 were resuspended in 100 µL of SIRT2 deacetylase buffer containing NAD (Sigma, St. Louis, Mo.) and [$^3$H] acetylated histone H4 peptide (a.a. 1-23) (Emiliani et al., 1998). TSA (WACO BioProducts, Richmond, Va.) was resuspended in dimethyl sulfoxide (DMSO) was further diluted in DMSO and added to reactions to desired concentration. Reactions were incubated for 2 hours at room temperature and stopped by the addition of 25 µL 0.1 M HCl and 0.16 M acetic acid. Released acetate was extracted in 500 µL ethyl acetate, and vortexed for 15 minutes. After centrifugation for 5 minutes, 400 µL of the ethyl acetate fraction was mixed with 5 ml scintillation fluid and counted.

Western Blotting

Samples were separated on 10% sodium dodecyl sulfate (SDS)-polyacrylamide gels and transferred to Hybond ECL nitrocellulose membrane (Amersham Pharmacia Biotech, Inc., Piscataway, N.J.). Membranes were blocked with 5% blocking reagent (Bio-Rad, Hercules, Calif.) in TBS-Tween (10 mM Tris, pH 7.5, 150 mM NaCl, and 0.1% Tween-20), they were probed with anti-acetylated tubulin 6-11B-1, anti-tubulin B-5-1-2 or anti-FLAG M2 (Sigma, St. Louis, Mo.) all at 1:2000 dilution or anti-living colors peptide antibody (Clontech, Mountain View, Calif.), anti-p65 (Santa Cruz Biotech, Santa Cruz, Calif.), or anti-Lamin A (Cell Signaling Technology, Inc., Beverly, Mass.) all diluted at 1:1000. Secondary detection was performed using horseradish peroxidase-coupled sheep anti-mouse IgG (Amersham Pharmacia Biotech, Inc., Piscataway, N.J.) or goat anti-rabbit IgG (Pierce Chemical Co., Rockford, Ill.) both diluted 1:5000 and ECL western blotting detection system (Amersham Pharmacia Biotech, Inc., Piscataway, N.J.).

Immunofluorescence

HeLa cells grown on coverslips were transfected with LipofectAMINE reagent (Gibco Invitrogen Corp., Carlsbad, Calif.) for 8 hours according to manufacturer's protocol or by calcium phosphate DNA precipitation method. Transfected cells were incubated for 12 hours with 400 nM TSA (WACO BioProducts, Richmond, Va.) 24 hours after transfection. Cells were washed twice for 10 minutes in PBS and fixed for 10 minutes in 4% formaldehyde (EMS, Ft. Washington, Pa.) followed by permeabilization for 10 minutes in 0.5% Triton-X-100 in PBS. Following three washes for 10 minutes in PBS, cells were incubated for 10 minutes in 10% BSA, and incubated for 1 hour with anti-acetylated tubulin 6-11B-1, anti-tubulin B-5-1-2 diluted 1:1000, or anti-FLAG M2 diluted 1:500 in 0.1% TWEEN-20™ non-ionic detergent. Cells were washed three times in 0.1% TWEEN-20™ non-ionic detergent, followed by incubation with goat anti-mouse IgG (Fc specific) TRITC-conjugated antibody (Sigma, St. Louis) diluted 1:100 in 0.1% TWEEN-20™ non-ionic detergent. Following incubation cells were incubated for 5 minutes in 20 mg/ml 4',6'-diamidino-2-phenylindole hydrochloride (DAPI) washed three times in phosphate-buffered saline (PBS), once in $ddH_2O$, and mounted with Gel Mount (Biomeda Corp., Foster City, Calif.). Slides were visualized on a Nikon E600 microscope system equipped with a SPOT 2 Digital Camera. Confocal images were acquired by laser-scanning confocal microscopy with an Olympus BX60 microscope equipped with a Radiance 2000 confocal setup (BioRad, Hercules, Calif.).

In Vitro Deacetylation Assay

Immunoprecipitations were resuspended in 100 µl SIRT deacetylase buffer containing 50 µg total cellular lysate from untransfected HEK 293T cells and 1 mM NAD. Reactions containing 400 nM TSA or 5 mM nicotinamide (Sigma, St. Louis, Mo.) were pre-incubated at room temperature with all components of the reaction in the absence of NAD for 10 minutes, Following the pre-incubation, the enzymatic reactions were started with the addition of NAD followed by incubation for 2 hours at room temperature with constant agitation. Reactions were stopped by the addition of 50 µl 6× SDS-polyacrylamide gel electrophoresis (PAGE) buffer. Beads were pelleted by centrifugation at 14,000 rpm for 10 minutes and 10 µl of each supernatant was separated on 10% SDS-PAGE gels and western blotted as described above.

Tubulin and Histone H3 Peptide Kinetics with Hst2p and SIRT2

Increasing concentrations of tubulin peptide (20-900 µM), and 800 µM NAD were reacted in the presence of 0.8 to 1 µM recombinant SIRT2 in 50 mM Tris, pH 7.5, 1 mM DTT, and 10% methanol at 37° C. For Hst2p reactions, tubulin peptides and 500 µM NAD were reacted in the presence of 9 to 19 µM recombinant Hst2p under the same conditions. Reactions were quenched with trifluoroacetic acid (TFA) to a final concentration of 1%. Time points were chosen such that initial velocity conditions were observed. Samples were injected into the high performance liquid chromatography (HPLC) with a Beckman C18 analytical column. Upon injection, the system was run isocratically with solvent A (0.05% TFA in $H_2O$), followed by a gradient of 0-10% solvent B (0.02% TFA in $CH_3CN$) for 4 minutes, and followed by a gradient of 10-23% solvent B for 23 minutes. Deacetylated and acetylated peptides eluted at 16% and 18% $CH_3CN$, respectively. Elution of substrates and products were monitored by measuring the absorbance at 214 nM, and corresponding peaks were integrated using the Beckman System Gold Nouveau software. The amount of product was quantified by calculating the percentage of the deacetylated tubulin peptide from the total tubulin peptide based upon their integration values. Graphs of rate versus tubulin peptide concentrations were fitted to the Michaelis-Menten equation to obtain the kinetic parameters of $K_m$, $k_{cat}$, and V/K.

The monoacetylated histone H3 peptide ARTKQTARK-STGG(AcK)APRKQL (SEQ ID NO:03) (AcLys-14H3) was utilized as substrate for both Hst2p and SIRT2. H3 peptide was H-labeled using the histone acetyltransferase PCAF and purified as described previously (Tanner et al., 2000). Rate measurements utilized a charcoal-binding assay where 70 µL of HDAC reactions were quenched in 10 μL of charcoal (1:3 charcoal volume to glycine buffer volume) containing 2 M Glycine at pH 10.0. Reaction times were chosen (usually 2-5 minutes) such that steady-state initial velocities were maintained. Samples were immediately heated for ≥20 minutes to liberate free acetate from Ac-ADP ribose prior to centrifugation. The supernatant was treated to an additional 10 μL of charcoal slurry before determining the total free acetate liberated (by liquid scintillation counting). Data were converted to initial rates and fitted to the Michaelis-Menten equation $v_0=([E]_0 k_{cat} \bullet [S]/(K_m+[S])$. Control experiments indicated that [$^3$H]-Ac-Lys H3 peptide was not hydrolyzed nonenzymatically. Also, addition of activated charcoal (at all pH values and temperatures examined) immediately stopped the enzymatic reaction. Heating at high pH was only necessary to liberate acetate from the Ac-ADP ribose.

Core Histones and Tubulin Proteins as Substrates

Calf thymus core histones (Calbiochem, San Diego, Calif.), were acetylated using 7.5-10 mg/mL calf thymus histones, 100 μM AcCoA (~150 cpm/pmole, NEN), 10 μM PCAF, in [5 mM DTT, 50 mM, Tris, pH 7.5] for 1.5 h at 23° C. Remaining Acetyl-CoA was removed by gel-filtration and labeled histones were quantified by liquid scintillation counting. Deacetylation assays were performed using 30-50 nM enzyme, 500 μM NAD, ~1.2 μM histones, pH 7.5 and 24±1° C. Product formation was calculated from the radioactive charcoal-binding assay.

Microtubule Destabilizing Drug Treatments

HEK 293T, HeLa, and HepG2 cells were treated for 6 hours with 25 μM colchicines (Sigma) and lysed in low-stringency lysis buffer. Lysates were equilibrated by total protein concentration and were separated on 10% SDS-PAGE gels and western blotted as described above.

Results

Human SIRT2 Exhibits NAD-Dependent Histone Deacetylase Activity

To determine whether SIRT2 contained the NAD-dependent deacetylase activity associated with other SIR2 related proteins, E. coli purified recombinant SIRT2 was incubated with increasing concentrations of NAD and a peptide corresponding to the amino terminal tail of histone H4 (a.a. 1-23) acetylated in vitro.

FIGS. 1A-D depict NAD-dependent deacetylation of a histone peptide by human SIRT2. FIG. 1A. The enzymatic activity of recombinant 6-His-SIRT2 on a [$^3$H]acetylated histone H4 peptide (a.a. 1-23) was measured in the presence of increasing concentrations of NAD. Released acetate was extracted and measured by scintillation counting. FIG. 1B. The enzymatic activity of immunoprecipitated protein from FLAG or SIRT2-FLAG transfected HEK 293T cells on a [$^3$H] acetylated histone H4 peptide (a.a. 1-23) was measured in the presence of increasing concentrations of NAD. 10% of immunoprecipitated input into the enzymatic reaction was analyzed by SDS-PAGE and western blotting analysis with an anti-FLAG antibody. FIG. 1C. Similar reaction as described in (B) with SIRT2-FLAG -/+ NAD or HDAC6-FLAG and increasing concentrations of TSA. SDS-PAGE and western blotting analysis as described in (B). FIG. 1D. Similar reaction as described in (B) with SIRT2-FLAG -/+ NAD and increasing concentrations of nicotinamide. SDS-PAGE and western blotting analysis as described in (B).

A dose dependent increase in histone deacetylase (HDAC) activity was observed in response to increasing concentrations of NAD (FIG. 1A). A further increase in NAD concentration to 10 mM resulted in a reduction in deacetylase activity (FIG. 1A). Similarly, a FLAG epitope-tagged SIRT2 protein (SIRT2-FLAG) was immunoprecipitated after transfection of HEK 293T cells. SIRT2-FLAG showed a similar increase in HDAC activity in response to increasing concentrations of NAD from 1 μM to 1 mM (FIG. 1B). However, this HDAC activity further increased in response to NAD concentrations of 10 mM (FIG. 1B). Equivalent amount of SIRT2-FLAG was present in each reaction as demonstrated by western blotting analysis (FIG. 1B).

Our results confirm that SIRT2 contains NAD-dependent histone deacetylase activity as described previously (Tanner et al., 2000; Finnin et al., 2001). Furthermore, the observation that recombinant SIRT2 is enzymatically active indicates that the deacetylase activity of SIRT2 does not require associated factors (FIG. 1A). However, the presence of associated factors in cellular lysates could play a role in the increased activity observed in the presence of high concentrations of NAD (FIG. 1B).

In contrast to class I and class II deacetylases, class III deacetylases are reported to be insensitive to the potent class I and class II inhibitor Trichostatin A (TSA) (Yoshida et al., 1990; Furumai et al., 2001). To confirm that the SIRT2 enzymatic activity is insensitive to TSA, the enzymatic activity of immunoprecipitated SIRT2-FLAG with 1 mM NAD in the presence or absence of increasing concentrations of TSA (100-1600 nM) was measured. No change in HDAC activity of SIRT2 was measured in response to increasing concentrations of TSA (FIG. 1C). In contrast, HDAC6-FLAG immunoprecipitated from transfected HEK 293T was potently inhibited by 400 nM TSA (FIG. 1C).

Nicotinamide represents the first product from hydrolysis of the pyridinium-N-glycosidic bond of NAD (Landry et al., 2000) and functions as an effective inhibitor for the related SIRT1 protein (Luo et al., 2001). To test whether SIRT2 is also inhibited by nicotinamide, SIRT2-FLAG immunoprecipitated from transfected lysates was incubated with increasing concentrations of nicotinamide. A dose dependent decrease in HDAC activity was observed with increasing concentrations of nicotinamide ranging from 156 μM to 20 mM (FIG. 1D).

FIGS. 2A-C depict inactivation of SIRT2 histone deacetylase activity by point mutations within the SIRT2 catalytic domain. FIG. 2A. Schematic diagram of Sir2 proteins from S. cerevisiae, C. elegans, and Drosophila aligned with human SIRT2 within a region of the Sir2 domain (schematic adapted from (Frye, 1999)). Highlighted are two key residues necessary for histone deacetylase activity (Finnin et al., 2001). Genbank accession numbers of proteins described are: S. cerevisiae NP 010242, C. elegans NP 501912, D. melanogaster AAC79684, and human SIRT2 NP 036369. FIG. 2B. The enzymatic activity of immunoprecipitated protein from FLAG vector and SIRT2-FLAG wild-type, N152A, or H187Y mutants transfected HEK 293T cells on a [$^3$H] acetylated histone H4 peptide (a.a. 1-23) was measured with or without NAD. 10% of immunoprecipitation input into the enzymatic reaction was analyzed by SDS-PAGE and western blotting with an anti-FLAG antibody. FIG. 2C. The enzymatic activity of immunoprecipitated protein from GFP or GFP-SIRT2 wild-type, N152A, or H187Y mutants in assay as described in (B). SDS-PAGE and western blot as described in (B) using an anti-GFP antibody.

The Sir2 proteins contain a highly conserved domain, the Sir2 domain, associated with enzymatic activity. A number of highly conserved residues have been identified within this domain that are necessary for deacetylase activity (highlighted in FIG. 2A) (Finnin et al., 2001). To confirm the role of these residues in deacetylase activity, asparagine 168 was substituted with an alanine and histidine 187 with a tyrosine both within the context of SIRT2-FLAG and in a fusion protein between GFP and the N terminus of SIRT2 (GFP-SIRT2). It was demonstrated that both proteins immunoprecipitated with either anti-FLAG of anti-GFP, respectively, contain NAD-dependent activity (FIG. 2B,C). In both constructs, the N168A and H187Y substitutions abolished this observed HDAC activity (FIG. 2B,C).

Sub-Cellular Distribution of Human SIRT2

While class I HDACs remain exclusively nuclear, class II HDACs shuttle between the nucleus and cytoplasm. This nucleocytoplasmic shuttling is regulated by phosphorylation and represents an element in the regulation of their enzymatic activity (Fischle et al., 2001). Interestingly, class III HDACs exhibit variable sub-cellular distribution. Mouse Sir2α and its human homologue SIRT1 are localized primarily to the nucleus (Vaziri et al., 2001; Luo et al., 2001). In contrast, mouse and human SIRT2 are localized primarily to the cytoplasm (Afshar and Murnane, 1999; Yang et al., 2000), and interestingly the human SIRT3 protein is localized to mitochondria (Schwer et. al. submitted). The sub-cellular localization of SIRT2, both as a fusion protein with GFP and as a FLAG-tagged protein, was determined by two independent approaches. First, nuclear and cytoplasmic extracts from transfected HEK 293T cells were purified, and tested these extracts by western blotting with anti-GFP or anti-FLAG antibodies. GFP-SIRT2 was exclusively cytoplasmic whereas SIRT2-FLAG was predominately cytoplasmic with a small fraction present within the nuclear compartment. Probing of the same fractions for a known cytoplasmic protein, p65, and for a known nuclear protein, Lamin A, confirmed the purity of our cytoplasmic and nuclear fractions.

Second, immunofluoresence microscopy was used to further confirm the sub-cellular localization of SIRT2. After transfection of GFP-SIRT2 and SIRT2-FLAG into HeLa cells, an exclusively cytoplasmic localization for both fusion proteins was observed. Furthermore, it was noted that SIRT2 was locally more concentrated at an apolar axis of the nucleus. This localization pattern coincided with the characteristic increase in tubulin localization at the microtubule organization center (MTOC), also located at an apolar axis of the nucleus.

Tubulin Deacetylation by Human SIRT2 In Vivo

The localization of SIRT2 in a region corresponding to the MTOC enticed us to test whether SIRT2 can deacetylate tubulin. Following transfection of HeLa cells with GFP-SIRT2, which remains catalytically active as a deacetylase (FIG. 2C), cells were stained with an antiserum specific for α-tubulin acetylated at lysine-40 (Pipemo et al., 1987). It was found that cells expressing GFP-SIRT2 showed a marked reduction in acetylated tubulin in comparison to neighboring untransfected cells. As a control, cells transfected with an expression vector for GFP alone exhibited no alteration in the level of acetylated tubulin. Two possibilities were considered to explain these results. First, SIRT2 could be a bona fide tubulin deacetylase. Second, the active SIRT2 may regulate tubulin polymerization dynamics thus resulting in reduced polymerized microtubules, which may affect the acetylation state of α-tubulin. To answer this question, GFP-SIRT2 transfected cells were stained with an antisera that recognizes α-tubulin irrespective of the acetylation state. No visible change in the microtubule network was observed in cells transfected with GFP-SIRT2 in comparison to untransfected cells. These results are consistent with the model that SIRT2 is a functional tubulin deacetylase.

To verify that the deacetylase activity of SIRT2 was necessary for α-tubulin deacetylation, GFP-SIRT2 expression vectors containing our catalytically inactive mutations N168A and H187Y were transfected into HeLa cells. It was observed that catalytically inactive mutant SIRT2 had no effect on the level of acetylated α-tubulin. These results indicate that expression of wild-type SIRT2 in vivo leads to the deacetylation of lysine-40 on α-tubulin, mediated by the deacetylase activity of SIRT2.

Human SIRT2 Deacetylates Tubulin In Vitro

Figure 3B:
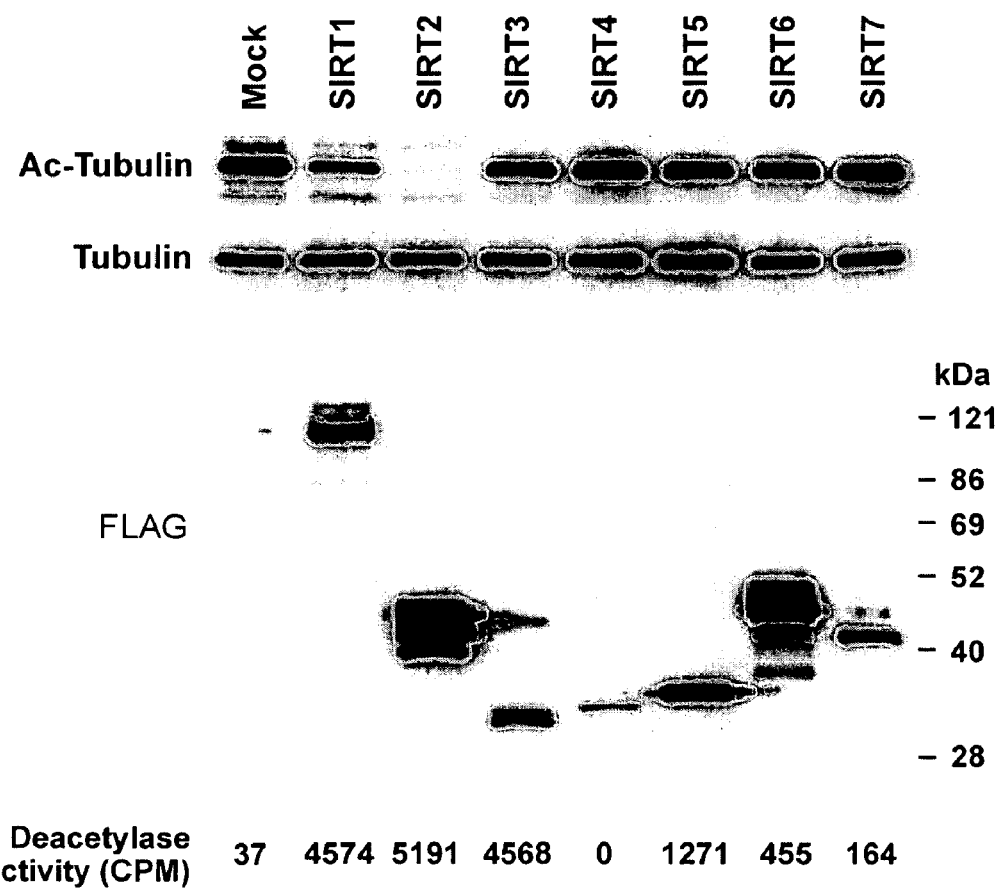

To test directly the ability of SIRT2 to deacetylate α-tubulin, an ex vivo tubulin deacetylation assay was developed. In this assay, HEK 293T cells were transfected with SIRT2-FLAG followed by immunoprecipitation of the FLAG-tagged protein (FIG. 3A). The immunoprecipitated material was separated into two fractions. The first fraction was used to measure HDAC activity using the acetylated histone H4 peptide. The second fraction was used for a tubulin deacetylation activity assay (FIG. 3A) using total cellular lysates from untransfected HEK 293T cells as substrate for acetylated α-tubulin. The extent of acetylation/deacetylation of α-tubulin was determined by western blotting analysis using a specific antisera for acetylated α-tubulin. First, it was demonstrated that material immunoprecipitated after transfection of HEK 293T cells with an empty FLAG vector has no effect on tubulin acetylation (FIG. 3B, lanes 1). This result demonstrates that neither the lysate utilized as acetylated α-tubulin substrate nor the immunoprecipitation procedure carry any significant levels of tubulin deacetylase activity. In contrast, incubation of cellular lysate with the immunoprecipitated SIRT2-FLAG protein deacetylated tubulin in an NAD-dependent manner (FIG. 3B, lanes 2 and 3). In addition, it was confirmed that the catalytically inactive mutants N168A and H187Y do not deacetylate α-tubulin (FIG. 3B, lanes 4 and 5).

Figure 3C:
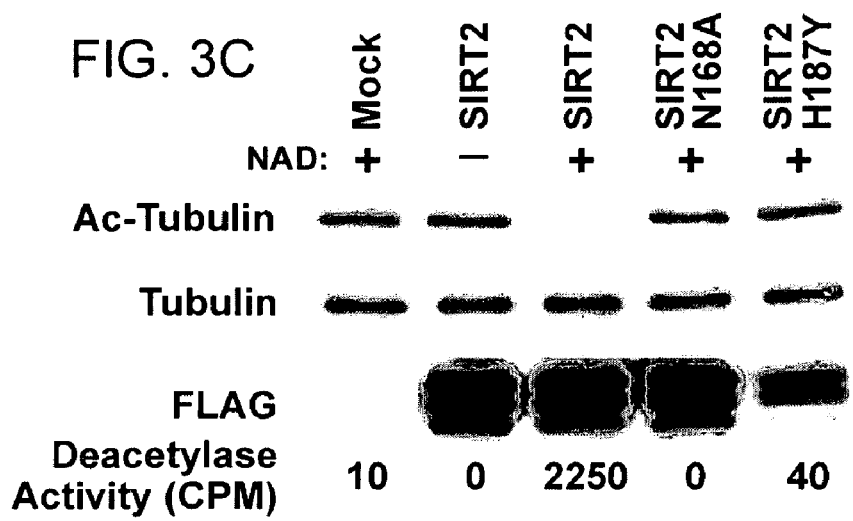

Humans contain seven highly conserved proteins with homology to S. cerevisiae Sir2p (Frye, 1999; Frye, 2000). To determine whether α-tubulin deacetylation activity was restricted to SIRT2, all seven human Sir2 proteins tagged with FLAG at the C-terminus were expressed in HEK 293T cells and immunoprecipitated. The immunoprecipitated material was tested both in our ex vivo tubulin deacetylation assay and in HDAC activity assay using the histone H4 peptide. Of the seven SIRT proteins, only SIRT1, 2 and 3 demonstrated significant HDAC activity on a histone H4 peptide (FIG. 3C). SIRT4,5,6, and 7 had no detectable HDAC activity (FIG. 3C). In contrast, only SIRT2 deacetylated tubulin in vitro (FIG. 3C). These results demonstrate that SIRT2 is the only class III deacetylase protein capable of deacetylation of tubulin.

Figure 3D:
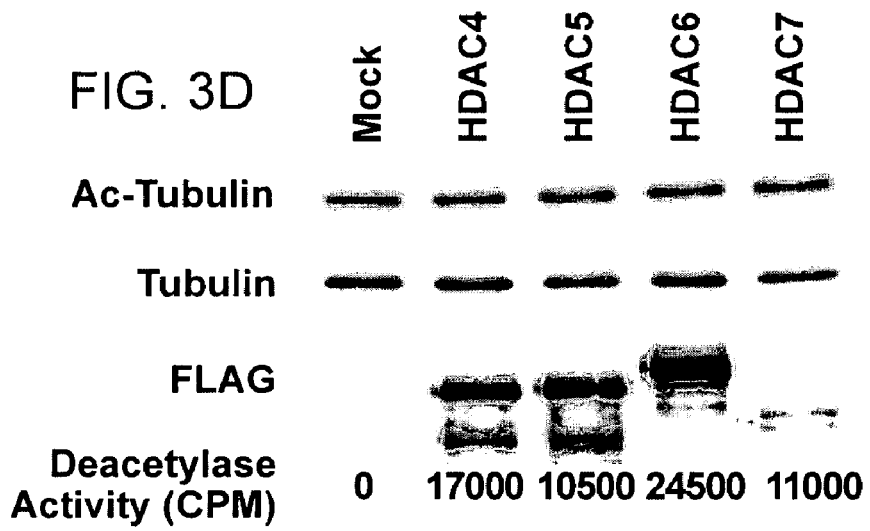

Treatment of cells with the class I and class II HDAC inhibitor TSA induces hyperacetylation of α-tubulin (Grozinger et al., 2001). This result suggest that a class I or class II HDAC can also deacetylate α-tubulin. Since class I HDACs are exclusively nuclear, the class II HDACs, which are know to shuttle between the nucleus and cytoplasm, were focused on. HDAC4,5,6, and 7 FLAG-tagged at the C-terminus, were transfected in HEK 293T, immunoprecipitated and tested both for HDAC activity and for tubulin deacetylase activity. All class II HDACs showed abundant deacetylase activity on the acetylated H4 peptide (FIG. 3D). However, none of the class II HDACs tested contained tubulin deacetylase activity (FIG. 3D).

Figure 3E:

Purification of a SET3 complex from S. cerevisiae has identified both class I and class III HDACs present in the same multi-protein complex (Pijnappel et al., 2001). To confirm that a SIR2-like protein is the sole component in the immunoprecipitation responsible for tubulin deacetylation, it was tested whether nicotinamide could inhibit the tubulin deacetylase activity associated with SIRT2. HEK 293T cells were transfected with SIRT2-FLAG or the empty vector as a control, followed by immunoprecipitation using anti-FLAG. No deacetylation was noted in the absence of NAD (FIG. 3E, lanes 2). Addition of NAD to the SIRT2-FLAG reaction led to the complete deacetylation of tubulin. This reaction was completely inhibited in the presence of 5 mM nicotinamide (FIG. 3E, lanes 3 and 4). As a control, Trichostatin A, a potent inhibitor of class I and class II HDACs, had no effect on tubulin deacetylation by SIRT2 (FIG. 3E, lane 5). These results confirm that the sole tubulin deacetylase found within the immunoprecipitated SIRT2 material is SIRT2.

FIGS. 3A-E depict SIRT2 tubulin deacetylates tubulin ex vivo. FIG. 3A. Schematic diagram of ex vivo tubulin deacetylation assay. FIG. 3B. Immunoprecipitated protein corresponding to SIRT2-FLAG wild-type, N168A, or H187Y, was incubated with cellular lysate in vitro. The reaction products were separated by SDS-PAGE and western blotting using specific antisera for acetylated tubulin, tubulin and FLAG. One half of immunoprecipitation was subjected to HDAC activity assay using a histone H4 peptide acetylated in vitro. FIG. 3C. Similar tubulin deacetylation assay using the seven class III HDACs, SIRT1-7-FLAG, as described for (B). One half of immunoprecipitation was subjected to HDAC activity assay as described for (B). FIG. 3D. Similar tubulin deacetylation assay using the class II HDACs as described for (B). One half of immunoprecipitation was subjected to HDAC activity assay as described for (B). FIG. 3E. Inhibition of SIRT2 tubulin deacetylation was examined using the similar tubulin deacetylation assay with SIRT2-FLAG as in (B) including reactions incubated with either 5 mM nicotinamide or 400 nM TSA.

Enzymatic Kinetics of Human SIRT2 and Yeast Hst2p

To further analyze the deacetylation of tubulin by SIRT2, a detailed enzymatic analysis was performed. For comparison, the highly active yeast histone deacetylase Hst2p was analyzed alongside the human enzyme. Hst2p exhibits strong selectivity for peptides corresponding to histone H3 acetylated on lysine-14 (Tanner et al., 2000; Landry et al., 2000). A 9-amino acid synthetic α-tubulin peptide (MPSD(AcK)TIGG; SEQ ID NO:08), acetylated on lysine-40 and a 20-amino acid synthetic histone H3 peptide (ARTKQTARKSTGG(AcK)APRKQL; SEQ ID NO:03), acetylated on lysine-14, were utilized to measure initial velocities of Hst2p and SIRT2 at various histone H3 or tubulin peptide concentrations. The resulting saturation curves were fitted to the Michaelis-Menten equation, yielding the kinetic parameters $k_{cat}$, $K_m$, and V/K. The $K_{cat}$ value is the maximal rate of enzyme turnover when substrates are at saturating concentrations. The $K_m$ value is the concentration of substrate needed to reach ½ the maximal velocity. The most physiologically relevant constant is the V/K value, as this second-order constant defines the rate of the reaction when substrate concentrations are not at saturating levels, and reflects both substrate binding and catalysis. Because cellular enzymatic reactions rarely occur under maximal velocity conditions (i.e. saturating substrate levels), dramatic differences in the V/K value of the enzyme will likely reflect the most relevant in vivo consequences.

With acetylated tubulin peptides as substrate, SIRT2 exhibited a striking preference for this substrate relative to yeast Hst2p (FIG. 4A). This difference was ~60-fold and was reflected in both the $k_{cat}$ and V/K values, which were 0.144±0.005 s$^{-1}$ and 894±100 M$^{-1}$s$^{-1}$ for SIRT2, and 0.00254±0.0003 s$^{-1}$ and 14.9 M$^{-1}$ s$^{-1}$ for Hst2p, respectively.

In contrast, when acetylated H3 peptide was employed as substrate, Hst2p demonstrated a ~200-fold stronger preference for H3 peptide relative to SIRT2 (FIG. 4B). These differences were reflected in the V/K and $K_m$ values, which were 3930±261 M$^{-1}$ s$^{-1}$ and 54.2±3.6 µM for SIRT2, and 717,900±35,900 M$^{-1}$s$^{-1}$ and 0.280±0.014 µM for Hst2p, respectively. The $k_m$ values (~0.2 s$^{-1}$) were similar between the two enzymes.

These results indicate that the Sir2-family of NAD-dependent deacetylases display remarkable differences in substrate specificity, and that human SIRT2 displays a marked preference for the acetylated tubulin peptide relative to the yeast enzyme Hst2p (FIGS. 4A, C, and D). To provide further evidence that SIRT2 has reduced capacity to deacetylate histones in comparison to Hst2p, the ability of SIRT2 and Hst2p to deacetylate core histones was examined. Purified histones acetylated in vitro by PCAF were incubated with catalytic amounts of either SIRT2 or Hst2p, and deacetylation was quantified (FIG. 4C). The apparent V/K values were determined and compared. Consistent with the peptide results, Hst2p exhibited a 7-fold higher V/K value than SIRT2.

FIGS. 4A-D depict the substrate preference for SIRT2. FIG. 4A. Initial velocities measured at varying concentrations of tubulin peptide, (MPSD(AcK)TIGG) for SIRT2 (open circles) and for Hst2p (closed circles) with concentrations and conditions described in materials and methods. The curve with SIRT2 represents the average rates from 3 different experiments. The Hst2p curve is a representative data set from 1 of 3 separate experiments. The indicated NAD concentrations are saturating with respect to each enzyme.

FIG. 4B. Initial velocities for each enzyme measured at varying concentrations of acetylated H3 peptide, (ARTKQTARKSTGG(AcK)APRKQL; SEQ ID NO:03) for SIRT2 (open circles) and for Hst2p (closed circles) with concentrations and conditions described in materials and methods. The indicated NAD concentrations are saturating with respect to each enzyme.

FIG. 4C. Kinetic progress curves of histone deacetylation by SIRT2 and Hst2p. Either SIRT2 (50 nM) or Hst2p (20 nM) were incubated with ~1.2 µM PCAF-acetylated calf thymus core histones.

FIG. 4D. Table listing the results when the graphs from (A) and (B) were fitted to the Michaelis-Menten equation to obtain the kinetic parameters of $K_m$, $k_{cat}$, and V/K.

Regulation of MIZ-1 Microtubule Binding by α-Tubulin Acetylation

A recent report documented the sequestration of the transcription factor, Myc-interacting zinc finger 1 (MIZ-1), by binding to tubulin on polymerized microtubules (Ziegelbauer et al., 2001). In this report, the authors suggest that upon depolymerization of the microtubule network, MIZ-1 is released by its binding tubulin and is free to translocate to the nucleus. Interestingly when the polymerization state of tubulin was interrogated by treatment with either colchicine or nocodazole, tubulin deacetylation in response to depolymerization by both treatments was observed (FIG. 5A). In addition, It was observed that only polymerized microtubules can serve as a substrate for acetylation of α-tubulin by the yet undefined tubulin acetyltransferase. In their report, Ziegelbauer et al., demonstrate that in the hepatocellular carcinoma cell line, HepG2, MIZ-1 has a predominately cytoplasmic localization. Interestingly, when the localization of GFP-MIZ-1 in HeLa cells, which have a low level of acetylated α-tubulin, was examined, it was found that it is predominately localized to the nucleus. However, when these cells were treated with TSA, which leads to hyperacetylation of tubulin, a distinct shift in localization of GFP-MIZ-1 from the nucleus to the cytoplasm was observed.

To determine if this relocalization of MIZ-1 to the cytoplasm upon treating cells with TSA is dependent on the acetylation state of α-tubulin, the deacetylase activity of SIRT2 was utilized. Upon co-transfection of cells with GFP-MIZ-1 and either the FLAG vector, SIRT2-FLAG wild-type or the catalytically inactive N168A mutant of SIRT2-FLAG, it was noticed that in all cases GFP-MIZ-1 localized predominately to the nucleus (FIG. 5B). However upon treatment of these cells upon TSA, a statistically significant relocalization of GFP-MIZ-1 into the cytoplasm was seen when GFP-MIZ-1 was co-transfected with either the FLAG empty vector or the catalytically inactive SIRT2-FLAG N168A of 36.9% and 35.3%, respectively (FIG. 5B). However when the GFP-MIZ-1 was co-transfected with SIRT2-FLAG wild-type a significant decrease in percentage of cells with GFP-MIZ-1 localized in the cytoplasm to 11.2% was seen (FIG. 5B). In their report, Ziegelbauer et al., demonstrate co-localization of MIZ-1 with the microtubule network in HepG2 cells, where MIZ-1 is apparently localized predominately in the cytoplasm.

As demonstrated above, in HeLa cells, GFP-MIZ-1 is localized primarily in the nucleus. To rule out the possibility is that the GFP-tagged version of MIZ-1 was altering MIZ-1 ability to bind to tubulin the sub-cytoplasmic localization in cells co-transfected with GFP-MIZ-1 and empty FLAG vectors and treated with TSA was assayeds. A colocalization of GFP-MIZ-1 with acetylated tubulin was visualized by confocal microscopy. This colocalization indicates that GFP-MIZ-1 maintains the ability to bind to tubulin, and indicates that upon treatment of transfected cells with TSA, GFP-MIZ-1 will translocate from the nucleus to the cytoplasm where it will bind to the hyperacetylated microtubule network. These data suggest that MIZ-1 sub-cellular distribution is regulated not only by the state of tubulin polymerization, but also by the acetylation state of α-tubulin within the microtubule network.

FIGS. 5A and 5B depict regulation of MIZ-1 sub-cellular distribution by acetylated tubulin.

FIG. 5A. HeLa, 293T and HepG2 cells were treated with 10 μg/mL colchicine or 1 μg/mL nocodazole for 6 hours. Cells were harvested and lysates separated by SDS-PAGE and western blotting using specific antisera for acetylated tubulin and tubulin.

FIG. 5B. Transfected cells were counted as either GFP-MIZ-1 localized completely nuclear or with partial cytoplasmic retention. Cell counts were derived from inspection of at least 150 transfected cells from six microscopic fields. Results are average of three separate transfections with error bars representing standard deviation between each transfection. Data set is representative of three independent experiments.

Example 2

Inhibition of SIRT2

Based on the dependency of SIRT proteins on NAD, a number of molecules with structure homology to NAD were tested as potential inhibitors of their enzymatic activity. The previously characterized molecule of 1-β-D-Ribofuranosyl-1-2-4-triazole-3-carboxamide (Ribavirin) has been used as an approved antiviral agent against hepatitis C and is an analog of the nicotinamide portion of NAD.

Inhibitory activity of ribavirin against SIRT2 and SIRT3 proteins was tested using recombinant SIRT2 proteins and an in vitro assay. Ribavirin was incubated with recombinant protein only in buffer for 10 minutes; then NAD and substrate were added to start the reaction. Reactions were incubated for 2 hours at room temperature. Reactions were stopped by adding 25 μL stop buffer (0.1M HC1, 0.16M acetic acid) and vortexing briefly. Ethyl acetate extraction isolated any liberated acetyl groups. Ethyl acetate (0.5 ml) was added, mixture was vortexed for 15 seconds and spun at 14,000 rpm for 5 minutes. The upper phase (0.4 ml) was added to 5 mL scintillation fluid (Econofluor-2; Packard) and counted.

Figure 7:
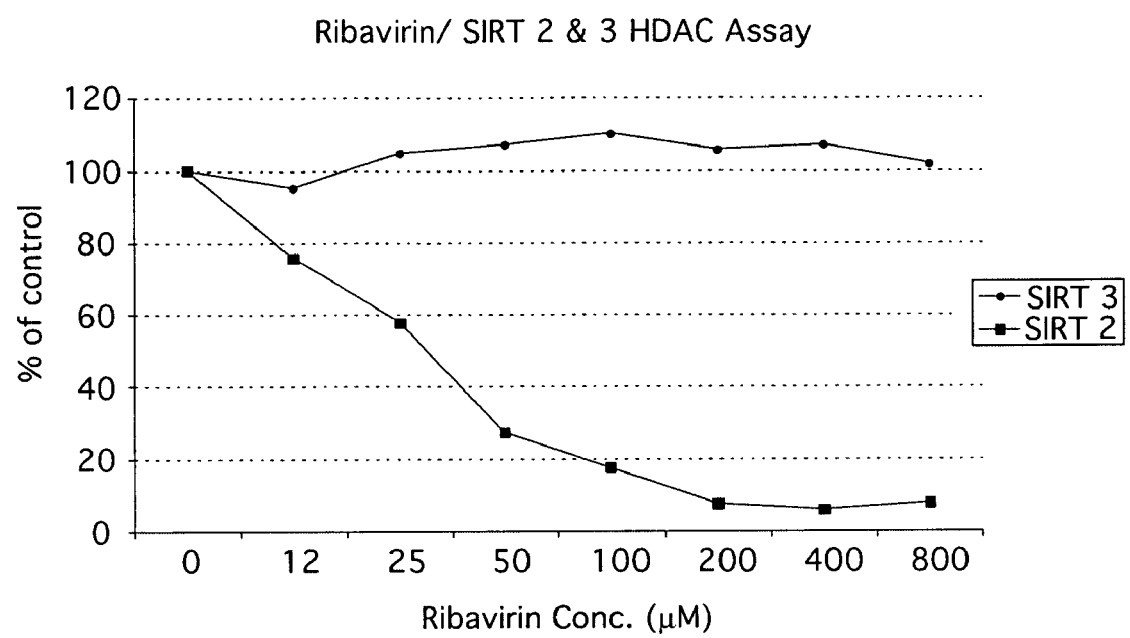
FIG. 7 depicts ribavirin inhibition of SIRT2.

The results are shown in FIG. 7. Ribavirin inhibited SIRT2 in vitro HDAC activity with an approximate 50% inhibition at 25 μM, but had no effect on SIRT3 in vitro HDAC activity. This experiment demonstrates the identification of a novel and specific inhibitor for SIRT2.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of inhibiting human sirtuin type 2 (SIRT2) tubulin deacetylase activity in a subject, the method comprising administering to the subject an agent that inhibits human SIRT2 sirtuin type 2 (SIRT2) tubulin deacetylase enzymatic activity, wherein the agent is administered in an amount effective to reduce SIRT2 tubulin deacetylase enzymatic activity by at least 10% relative to the level of SIRT2 tubulin deacetylase enzymatic activity in the absence of the agent, wherein the agent comprises ribavirin.

2. The method of claim 1, wherein the ribavirin is administered to the subject by oral administration.

3. The method of claim 1, wherein the ribavirin is administered to the subject at a dose of from about 30 mg to about 1200 mg per day.

4. The method of claim 1, wherein the subject has cancer.

5. The method of claim 4, wherein the cancer is a carcinoma, a sarcoma, a leukemia, or a lymphoma.

6. The method of claim 4, wherein the agent that inhibits SIRT2 tubulin deacetylase enzymatic activity reduces the level or rate of cell proliferation by at least 10% relative to the level or rate of cell proliferation in the absence of the agent.

7. The method of claim 4, wherein the agent that inhibits SIRT2 tubulin deacetylase enzymatic activity reduces tumor mass by at least 10% relative to the tumor mass in the absence of the agent.

8. The method of claim 1, wherein the agent that inhibits SIRT2 tubulin deacetylase enzymatic activity is administered in combination with a second therapy.

9. The method of claim 8, wherein the second therapy comprises chemotherapeutic treatment.

10. The method of claim 9, wherein the chemotherapeutic treatment comprises a cytotoxic or a cytostatic agent.

11. The method of claim 9, wherein the chemotherapeutic treatment comprises a chemotherapeutic agent selected from: an alkylating agent; a nitrosourea; an antimetabolite; an anti-tumor antibiotic; a vinca alkaloid; and a steroid hormone.

12. The method of claim 8, wherein the agent that inhibits SIRT2 tubulin deacetylase enzymatic activity is administered as an adjuvant to a standard cancer therapy.

13. The method of claim 8, wherein the second therapy comprises treatment with an antineoplastic agent.

14. The method of claim 13, wherein the anti-neoplastic agent comprises an antineoplastic agent selected from: an alkylating agent; an antimetabolite; a vinca alkyloid; an antineoplastic antibiotic; a platinum complex; a tyrosine kinase inhibitor; an inhibitor of a receptor tyrosine kinase that is involved in a growth factor signaling pathway; an inhibitor of a non-receptor tyrosine kinase involved in a growth factor signaling pathway; a serine/threonine kinase inhibitor; an inhibitor of a kinase involved in cell cycle regulation; a taxane; a tumor-associated antigen antagonist; and a tumor growth factor antagonist.

* * * * *

UNITED STATES PATENT AND TRADEMARK OFFICE
CERTIFICATE OF CORRECTION

PATENT NO. : 7,884,081 B2
APPLICATION NO. : 12/029333
DATED : February 8, 2011
INVENTOR(S) : Eric M. Verdin et al.

Page 1 of 1

It is certified that error appears in the above-identified patent and that said Letters Patent is hereby corrected as shown below:

Title Page item 54 and Col. 1

- In the title: Please delete the word "DEACETYLAST" and replace with "DEACETYLASE"; and Col. 53 line 31

- In claim 1: Please delete "sirtuin type 2 (SIRT2)"

Signed and Sealed this
Thirty-first Day of January, 2012

David J. Kappos
*Director of the United States Patent and Trademark Office*